(12) United States Patent
Chan

(10) Patent No.: US 11,473,121 B2
(45) Date of Patent: Oct. 18, 2022

(54) YEAST CONCENTRATION AND VIABILITY MEASUREMENT

(75) Inventor: Leo L. Chan, North Andover, MA (US)

(73) Assignee: NEXCELOM BIOSCIENCE LLC, Lawrence, MA (US)

( * ) Notice: Subject to any disclaimer, the term of this patent is extended or adjusted under 35 U.S.C. 154(b) by 3176 days.

(21) Appl. No.: 13/699,647

(22) PCT Filed: Jun. 6, 2011

(86) PCT No.: PCT/US2011/039216
§ 371 (c)(1),
(2), (4) Date: Sep. 4, 2013

(87) PCT Pub. No.: WO2011/156249
PCT Pub. Date: Dec. 15, 2011

(65) Prior Publication Data
US 2014/0024074 A1   Jan. 23, 2014

Related U.S. Application Data

(60) Provisional application No. 61/351,984, filed on Jun. 7, 2010.

(51) Int. Cl.
*C12Q 1/06* (2006.01)
*C12Q 1/64* (2006.01)
*C12Q 1/04* (2006.01)

(52) U.S. Cl.
CPC ............. *C12Q 1/06* (2013.01); *C12Q 1/04* (2013.01); *C12Q 1/64* (2013.01); *G01N 2333/39* (2013.01)

(58) Field of Classification Search
CPC ......... C12Q 1/06; C12M 1/34; C12M 1/3476; C12M 41/36; C12N 1/15; C12N 1/165; C12N 1/14; C12N 1/145
See application file for complete search history.

(56) References Cited

U.S. PATENT DOCUMENTS

2002/0168630 A1*  11/2002  Fleming ................... C12Q 1/06
435/5

FOREIGN PATENT DOCUMENTS

EP          1688740 A1 *  8/2006  ......... G01N 15/1056

OTHER PUBLICATIONS

Zhang et al. "Quantification of *Saccharomyces cerevisiae* viability using BacLight" Biotechnology Letters 26: 989-992, 2004 (Year: 2001).*
East et al. "QD-Antibody Conjugates via Carbodiimide-Mediated Coupling: A Detailed Study of the Variables Involved and a Possible New Mechanism for the Coupling Reaction under Basic Aqueous Conditions" Langmuir 27, 13888-13896, 2011 (Year: 2011).*

* cited by examiner

*Primary Examiner* — Thane Underdahl
(74) *Attorney, Agent, or Firm* — Milstein Zhang & Wu LLC

(57) ABSTRACT

The invention generally relates to analyzing yeast viability. More particularly, the invention relates to efficient and effective methods and compositions for accessing and measuring viability and concentration of yeast cells.

26 Claims, 23 Drawing Sheets

Calcofluor white (200-2000 ms)

Mg-ANS (1000-2000 ms)

Acridine Orange (200-400 ms)

SYTO 9 (75 - 800 ms)

pH ~ 7.00 pH ~ 7.80 pH ~ 8.30 pH ~ 9.00 pH ~ 10.00 pH ~ 10.50 pH ~ 11.00 pH ~ 11.50

100 ug/ml 50 ug/ml 25 ug/ml 12 ug/ml 6 ug/ml

FERMENTATION 2

AO (LIVE)

PI (DEAD)

YEAST PROP

AO (LIVE)

PI (DEAD)

pH 10-12.5 buffer

AO (LIVE)

PI (DEAD)

pH 10-12.5 buffer

AO (LIVE)

PI (DEAD)

YEAST CONCENTRATION AND VIABILITY MEASUREMENT

TECHNICAL FIELDS OF THE INVENTION

The invention generally relates to analyzing yeast viability. More particularly, the invention relates to efficient and effective methods and compositions for accessing and measuring viability and concentration of yeast cells.

BACKGROUND OF THE INVENTION

Biofuel development and production have dramatically increased over the last twenty to thirty years. With the continuing depletion of fossil fuels and increasing concern of global warming, large scale biofuel production has been introduced in Brazil, United States, and many other European countries to facilitate the replacement for a renewable energy source. Currently, the largest biofuel process relies heavily on ethanol production, which utilizes the baker's yeasts, *Saccharomyces cerevisiae*, to perform fermentation on sugar cane, corn meal, polysaccharides, and waste water. Due to their high ethanol tolerance, final ethanol concentration, glucose conversion rate, and the historical robustness of industrial fermentation, yeasts are the ideal component for bioethanol production. (Antoni, et al., "Biofuel from microbes," *Applied Microbiology Biotechnology*, vol. 77, pp. 23-35, 2007; Vertès, et al., "Technological Options for Biological Fuel Ethanol," *Journal of Molecular Microbiology and Biotechnology*, vol. 15, pp. 16-30, 2008; Basso, et al., "Yeast selection for fuel ethanol production in Brazil," *FEMS Yeast Research*, vol. 8, pp. 1155-1163, 2008; Nikolić, et al., "Effect of different fermentation parameters on bioethanol production from corn meal hydrolyzates by free and immobilized cells of *Saccharomyces cerevisiae* var. *ellipsoideus*," *Journal of Chemical Technological Biotechnology* vol. 84, pp. 497-503, 2009; Gibbons, et al., "Integrated biorefineries with engineered microbes and high-value co-products for profitable biofuels production," *In Vitro Cellular & Developmental Biology-Plant*, vol. 45, pp. 218-228, 2009; Hu, et al., "Genetic Dissection of Ethanol Tolerance in the Budding Yeast *Saccharomyces cerevisiae*," *Genetics*, vol. 175, pp. 1479-1487, 2007; Argueso, et al., "Genome structure of a *Saccharomyces cerevisiae* strain widely used in bioethanol production," *Genome Research*, vol. 19, pp. 2258-2270, 2009; Eksteen, et al., "Starch Fermentation by Recombinant *Saccharomyces cerevisiae* Strains Expressing the a-Amylase and Glucoamylase Genes From *Lipomyces Kononenkoae* and *Saccharomycopsis fibuligera*," *Biotechnology and Bioengineering*, vol. 84, pp. 639-646, 2003.)

The standard yeast-based fermentation process in the United States utilizes glucose extracted from maize starch. Maize (entire plant including corn) is dry-grind processed and heated to 100° C. at pH 6 with α-amylase. The mash is cooled to 65° C. at pH 4.5 with glucoamylase to degrade the starch into glucose, which is then possible for wild type baker's yeast to digest. The final composition is then cooled to 32° C. and transferred to a fermenter, where yeast is added to initiate ethanol production. In general, the entire fermentation process requires approximately 48-72 h to reach a final ethanol concentration of 10-12%. The concentration and viability of the added yeasts are critical factors in obtaining the maximum ethanol generation. Therefore, methods for measuring yeast concentration and viability are extremely important in providing consistent ethanol output.

There are several methods for concentration and viability measurement of pure yeast samples, such as light and fluorescent microscopy using manual hemacytometer and flow cytometry. (Trevors, et al., "A Comparison of Methods for Assessing Yeast Viability," *Biotechnology Letters*, vol. 5, pp. 131-134, 1983; Hernlem, et al., "Dual Fluorochrome Flow Cytometric Assessment of Yeast Viability," *Current Microbiology*, p. Published Online, 2010; Chang, et al., "Flow cytometric quantitation of yeast a novel technique for use in animal model work and in vitro immunologic assays," *Journal of Immunological Methods*, vol. 211, pp. 51-63, 1998; Deere, et al., "Flow Cytometry and Cell Sorting for Yeast Viability Assessment and Cell Selection," *Yeast*, vol. 14, pp. 147-160, 1998; Bouchez, et al., "Physiological Significance of the Cytometric Distribution of Fluorescent Yeasts After Viability Staining," *Biotechnology and Bioengineering*, vol. 86, pp. 520-530, 2004; Malacrinó, et al., "Rapid detection of viable yeasts and bacteria in wine by flow cytometry," *Journal of Microbiological Methods*, vol. 45, pp. 127-134, 2001.) The manual hemacytometer is low-cost, but tedious and prone to human-error that leads to large inconsistency. (Ng, et al., "The Challenge to Measure Cell Proliferation in Two and Three Dimensions," *Tissue Engineering*, vol. 11, pp. 182-191, 2005; Szabo, et al., "Evaluation of an Automated Instrument for Viability and Concentration Measurements of Cryopreserved Hematopoietic Cells," *Laboratory Hematology*, vol. 10, pp. 109-111, 2004.) In contrast, flow cytometry automates data acquisition, but requires calibration beads for concentration measurement, and thorough cleaning procedures to prevent cross contamination between samples. In addition, the cost of flow cytometry instrumentation also prevents the development of a simple and cost-effective method for yeast concentration measurement. (Davey et al., "Flow Cytometry and Cell Sorting of Heterogeneous Microbial Populations: the Importance of Single-Cell Analyses," *Microbiological Reviews*, vol. 60, pp. 641-696, 1996; Michelson, "Flow Cytometry: A Clinical Test of Platelet Function," *Blood*, vol. 87, pp. 4925-4936, 1996.)

Although each method has its disadvantages, fluorescence detection can still provide relatively accurate concentration and viability measurements on pure yeast samples. (Henry-Stanley, et al., "Adaptation of FUN-1 and Calcofluor white stains to assess the ability of viable and nonviable yeast to adhere to and be internalized by cultured mammalian cells," *Journal of Microbiological Methods*, vol. 59, pp. 289-292, 2004; Zandycke, et al., "Determination of Yeast Viability Using Fluorophores," *Journal of American Society of Brewing Chemists*, vol. 61, pp. 15-22, 2003; King, et al., "Epifluorescent Method for Detection of Nonviable Yeast," *Journal of American Society of Brewing Chemists*, vol. 39, pp. 52-54, 1981; McCaig, "Evaluation of the Fluorescent Dye 1-Anilino-8-Naphthalene Sulfonic Acid for Yeast Viability Determination," *Journal of American Society of Brewing Chemists*, vol. 48, pp. 22-25, 1990; Nikolova, et al., "An Optimised Method for Investigation of the Yeast Viability by Means of Fluorescent Microscopy," *Journal of Culture Collections*, vol. 3, pp. 66-71, 2002; Zhang et al., "Quantification of *Saccharomyces cerevisiae* viability using BacLight," *Biotechnology Letters*, vol. 26, pp. 989-992, 2004; Slater, "Rapid Nuclear Staining Method for *Saccharomyces cerevisiae*," *Journal of Bacteriology*, vol. 126, pp. 1339-1341, 1976; Oh et al., "Rapid viability assessment of yeast cells using vital staining with 2-NBDG, a fluorescent derivative of glucose," *International Journal of Food Microbiology*, vol. 76, pp. 47-53, 2002; Lloyd et al., "Vigour, vitality and viability of microorganisms," *FEMS Microbiology Letters*, vol. 133, pp. 1-7, 1995; Rodriguez-Porrata, et al., "Vitality enhancement of the rehydrated active dry wine yeast," *International Journal of Food Microbiology*, vol. 126, pp. 116-122, 2008.)

However, it is more important to be able to accurately and efficiently measure these parameters during fermentation to ensure consistent process. A common characteristic in the previous publications is that all of the samples tested are either dehydrated yeasts or has been purified due to the fact that debris from messy samples can greatly disturb the consistency of counting methods using hemocytometer, flow cytometry, and fluorescence microscopy. The methods described above would pose great difficulty since the debris of corn mash inhibits technicians and flow cytometers to accurately measure concentration and viability. (Abbott et al., "Buffering capacity of whole corn mash alters concentrations of organic acids required to inhibit growth of *Saccharomyces cerevisiae* and ethanol production," *Biotechnology Letters*, vol. 26, pp. 1313-1316, 2004; Devantier, et al., "Characterization of very high gravity ethanol fermentation of corn mash. Effect of glucoamylase dosage, pre-saccharification and yeast strain," *Applied Microbiology and Biotechnology*, vol. 68, pp. 622-629, 2005.)

Previously published article on AO and PI has used both dyes at their optimum pH from 6.5-7.4, which is the most common pH for buffers that are biologically feasible for mammalian cells. In the bright-field regime, both manual and automatic method are hindered by debris in the imaging field, thus consistent measurements are often limited. Using fluorescence measurement to specifically detect yeasts in messy sample also posed an issue, due to nonspecific staining of debris in the solution. Furthermore, fluorescence detection would result in weak target cell signals and large nonspecific staining of corn mash debris. Only by a laborious filtration process that separates yeasts from corn mash could one utilize the methods above effectively. However, concentration and viability of yeast are more accurately represented when measured in their fermentation environment.

Therefore, there is an unmet need for measuring yeast viability in messy industrial samples. The invention presented here describes a novel method for detecting and measuring yeast concentration and viability using standard fluorescent stains and adjusting the pH of buffer.

SUMMARY OF THE INVENTION

The invention is based, in part, on the discovery of efficient and effective methods and compositions for accessing and measuring viability and concentration of yeast cells. The present invention addresses the shortcomings of the previous methods in that real time samples such as those from biofuel plants that contain corn mash and other debris may be readily and accurately analyzed by the methods of the invention. Messy samples can be effectively measured as the invention allows high staining specificity. Besides corn mash, viability of yeast in sugar cane fermentation can also be measured using this method.

In one aspect, the invention generally relates to a method for measuring a concentration of yeast cells. The method includes: staining a sample to be tested for yeast cell concentration with a dye under a buffer condition having a pH of about 10 to about 12.5; acquiring a fluorescent image of the dye-stained sample; analyzing the fluorescent image of the dye-stained sample to determine the concentration of viable yeast cells.

In another aspect, the invention generally relates to a method for determining yeast viability. The method includes: staining a sample to be tested for yeast viability with a first dye and with a second dye under a buffer condition having a pH of about 10 to about 12.5; acquiring a fluorescent image of the first dye-stained sample; acquiring a fluorescent image of the second dye-stained sample; and comparing the fluorescent image of the first dye-stained sample and the fluorescent image of the second dye-stained sample to determine yeast viability.

In yet another aspect, the invention relates to a method for determining the concentration of viable yeast cells. The method includes: staining a sample to be tested with a first dye and with a second dye under a buffer condition having a pH of about 10 to about 12.5; acquiring at least one static fluorescent image of the first dye-stained sample; acquiring at least one static fluorescent image of the second dye-stained sample; and analyzing the at least one static fluorescent image of the first dye-stained sample and the at least one static fluorescent image of the second dye-stained sample to determine the concentration of viable yeast cells in the sample.

In yet another aspect, the invention generally relates to a method for determining yeast viability. The method includes: staining a sample to be tested for yeast viability with a first dye and with a second dye under a buffer condition having a pH of about 10 to about 12.5; acquiring at least one static bright-field image and at least one static fluorescent image of the first dye-stained sample; comparing the at least one bright-field image to the at least one fluorescent image of the first dye-stained sample to determine a characteristic of viable yeast cells in the sample; acquiring at least one static bright-field image and at least one static fluorescent image of the second dye-stained sample; and comparing the at least one bright-field image to the at least one fluorescent image of the second dye-stained sample to determine a characteristic of non-viable yeast cells in the sample. The method may further include determining the concentration of viable yeast cells.

In yet another aspect, the invention generally relates to a method for determining the concentration of viable yeast cells. The method includes: staining a sample to be tested with a first dye and with a second dye under a buffer condition having a pH of about 10 to about 12.5; acquiring at least one static bright-field image and at least one static fluorescent image of the first dye-stained sample; acquiring at least one static bright-field image and at least one static fluorescent image of the second dye-stained sample; and determine the concentration of viable yeast cells in the sample.

In yet another aspect, the invention generally relates to a method for determining yeast viability. The method includes: staining a sample to be tested for yeast viability with Acridine Orange under a buffer condition of pH of about 10.5 to about 12.5; acquiring at least one static bright-field image of the Acridine Orange-stained sample by directing a bright-field light beam to the sample; acquiring at least one static fluorescent image of the Acridine Orange-stained sample by directing an excitation light beam to the sample; comparing the at least one bright-field image to the at least one fluorescent image of the Acridine Orange-stained sample to determine the characteristics of the viable yeast in the sample; staining a sample to be tested for yeast viability with Propidium Iodide under a buffer condition of pH of about 10.5 to about 12.5; acquiring at least one static bright-field image of the Propidium Iodide-stained sample by directing a bright-field light beam to the sample; acquiring at least one static fluorescent image of the Propidium Iodide-stained sample by directing an excitation light beam to the sample; comparing the at least one bright-field image to the at least one fluorescent image of the Propidium Iodide-stained sample to determine the characteristic of the non-viable yeast in the sample; and determining the yeast viability of the sample.

BRIEF DESCRIPTION OF THE DRAWINGS

The figures presented here are a series of rigorous fluorescent imaging analysis experiments to discover a working model for yeast viability measurement directly from fermenters, where the fluorescent reagents are not in the normal range of the optimized conditions.

DETAILED DESCRIPTION OF THE INVENTION

Figure 1:
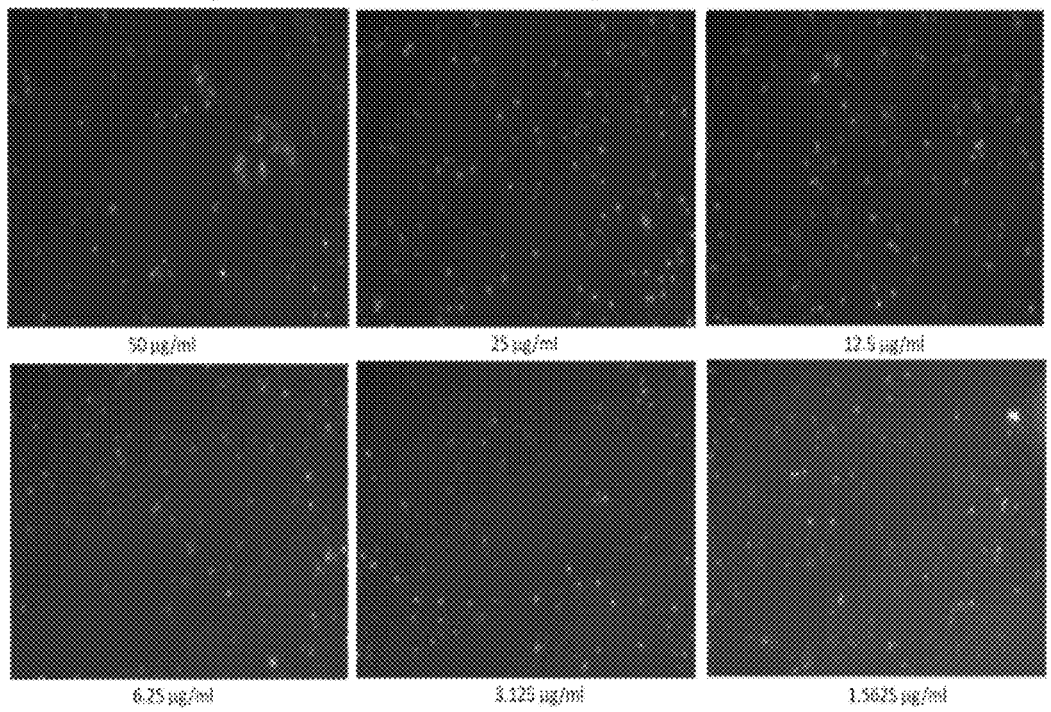
FIG. 1 depicts a series of 4 UV excited dyes at various concentrations, where fluorescence signals of yeasts are compared.
Figure 1:
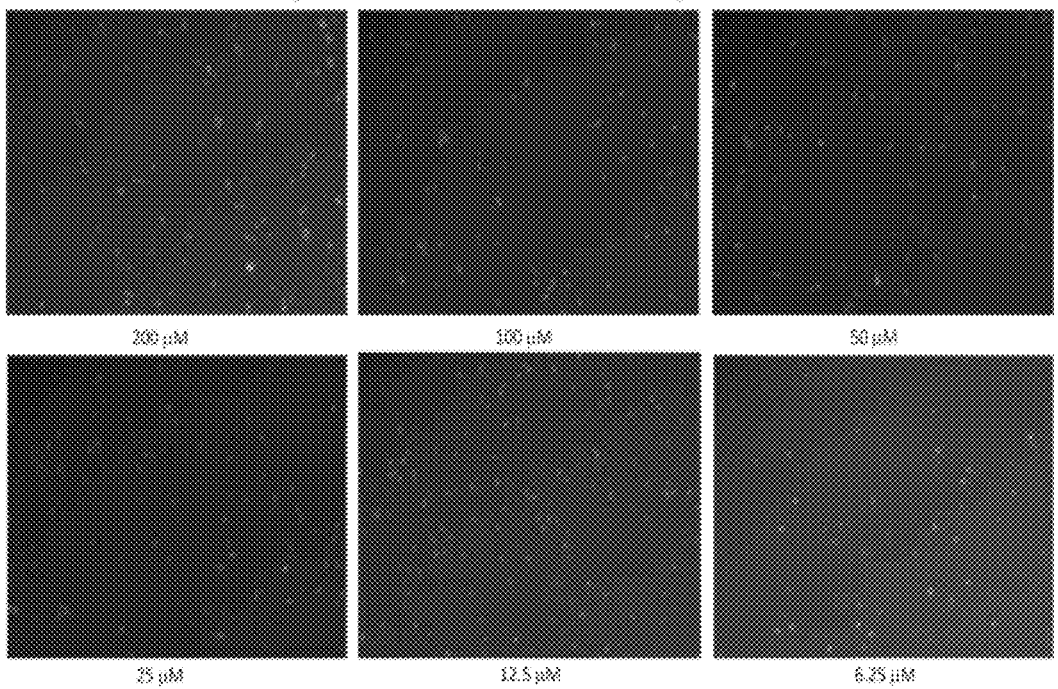
Figure 1:
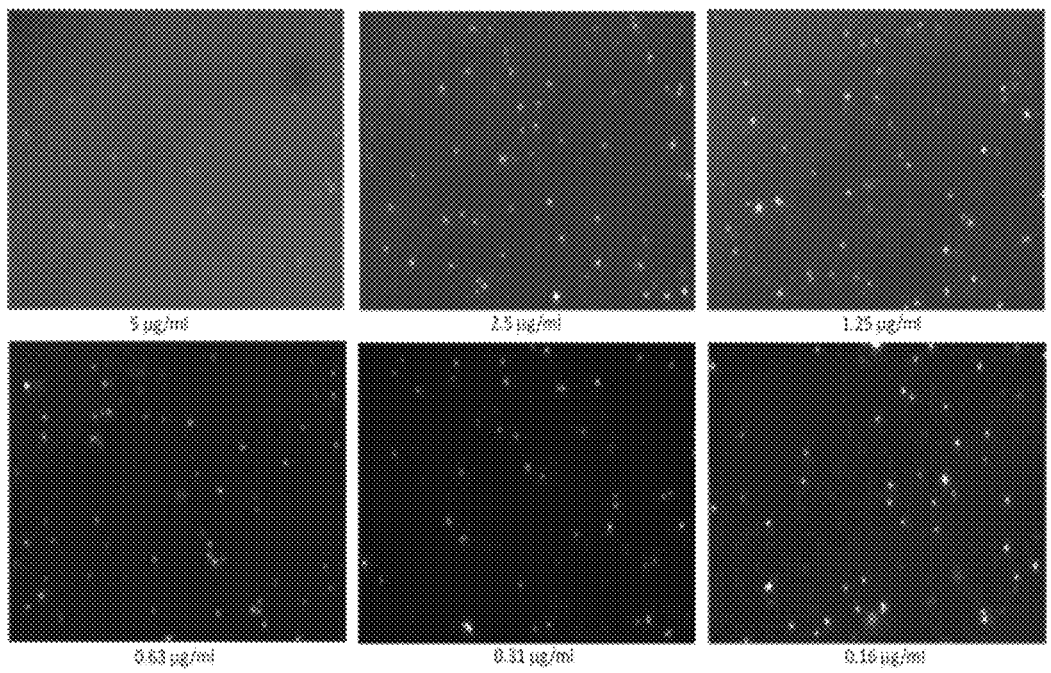
Figure 1:
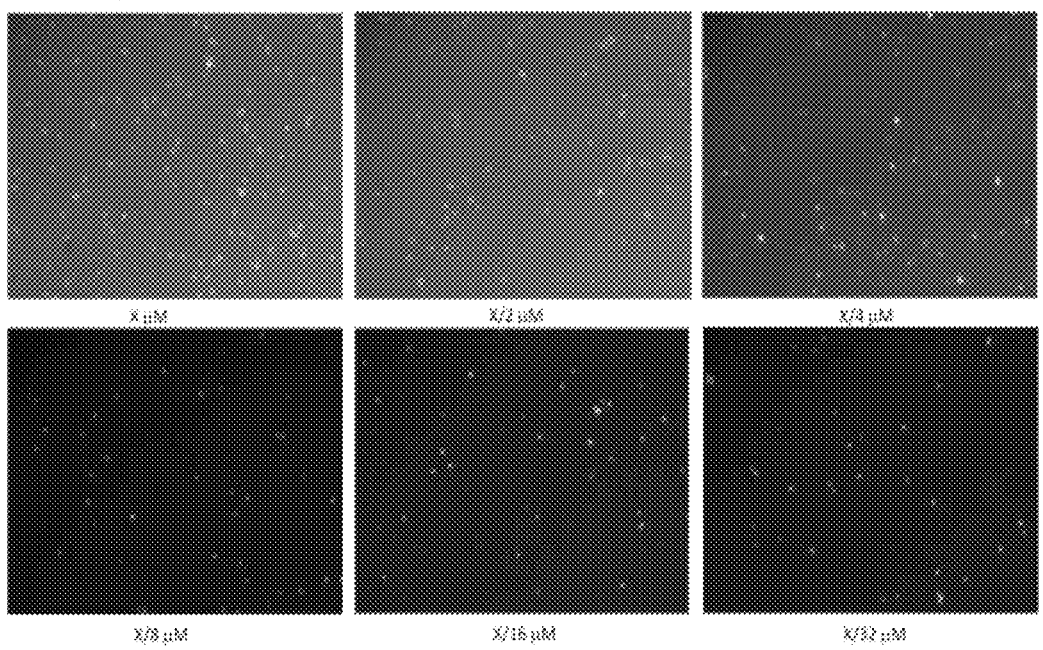

The present invention addresses the shortcomings of the previous methods in that real time samples such as those from biofuel plants that contain corn mash and other debris may be readily and accurately analyzed by the methods of the invention. Messy samples can be effectively measured as the invention allows high staining specificity. Therefore, the invention is based, in part, on the discovery of efficient and effective methods and compositions for accessing and measuring viability and concentration of yeast cells.

Recently, a novel imaging cytometry method has been developed by Nexcelom Bioscience (Lawrence, Mass.), which allows rapid measurement of cell concentration using inexpensive disposable counting chambers that require only 20 µl of samples. (Lai, et al., "Intratumoral Epidermal Growth Factor Receptor Antisense DNA Therapy in Head and Neck Cancer: First Human Application and Potential Antitumor Mechanisms," *Journal of Clinical Oncology*, vol. 27, pp. 1235-1242, March 2009; Nott, et al., "Genomic Responses from the Estrogen-responsive Element-dependent Signaling Pathway Mediated by Estrogen Receptor alpha Are Required to Elicit Cellular Alterations," *Journal of Biological Chemistry*, vol. 284, pp. 15277-15288, May 2009; Qiao, et al., "Thiol Oxidative Stress Induced by Metabolic Disorders Amplifies Macrophage Chemotactic Responses and Accelerates Atherogenesis and Kidney Injury in LDL Receptor-Deficient Mice," *Arteriosclerosis Thrombosis and Vascular Biology*, vol. 29, pp. 1779-U139, November 2009; Rounbehler, et al., "Targeting Ornithine Decarboxylase Impairs Development of MYCN-Amplified Neuroblastoma," *Cancer Research*, vol. 69, pp. 547-553, January 2009; Shanks, et al., "Quantitative PCR for Genetic Markers of Human Fecal Pollution," *Applied and Environmental Microbiology*, vol. 75, pp. 5507-5513, September 2009; Stengel, et al., "Identification and Characterization of Nesfatin-1 Immunoreactivity in Endocrine Cell Types of the Rat Gastric Oxyntic Mucosa," *Endocrinology*, vol. 150, pp. 232-238, January 2009.) Utilizing combined bright-field and fluorescent imaging, the system allows automated cell image acquisition and processing using a novel counting algorithm for accurate and consistent measurement of cell population and viability on a variety of cell types. Applications such as enumeration of immunological, cancer, stem, insect, adipocytes, hepatocytes, platelets, algae, and heterogeneous cells, quantification of GFP transfection, viability using Trypan Blue or Propidium Iodide, measuring WBCs in whole blood, have been previously reported. More importantly, the method has been shown to produce consistent concentration and viability measurements of pure yeast for quality control purposes in biofuel, beverage, and baking industry. (Nexcelom Bioscience, "Simpe, Fast and Consistent Determination of Yeast Viability using Oxonol," in *Application Focus: Cellometer Vision 10x*, pp. 1-2.)

Disclosed herein is a novel imaging fluorescence cytometry method employing the Cellometer® Vision (Nexcelom Bioscience) for determining yeast concentration and viability in corn mash from operating fermenters. Using a dilution buffer of the invention and staining the sample with Acridine Orange (AO) and Propidium Iodide (PI), the viable and nonviable yeasts are selectively labeled while nonspecific fluorescent signals from corn mash are eliminated. This method can efficiently perform yeast quality control using samples directly from processing fermenters without further filtration treatment, which can have a dramatic impact on monitoring consistent bioethanol production in the United States. Besides corn mash, viability of yeast in sugar cane fermentation can also be measured using this method.

In one aspect, the invention generally relates to a method for measuring a concentration of yeast cells. The method includes: staining a sample to be tested for yeast cell concentration with a dye under a buffer condition having a pH of about 10 to about 12.5; acquiring a fluorescent image of the dye-stained sample; analyzing the fluorescent image of the dye-stained sample to determine the concentration of viable yeast cells. The dye may be selected from the group consisting of Acridine Orange, SYTO 9, DAPI, Hescht, Calcofluor White, Propidium Iodide, Ethidium Bromide, Oxonol, Mg-ANS, for example. In some embodiments, the dye is Acridine Orange having a concentration of about 1 µg/mL to about 5 µg/mL (e.g., from about 1 µg/mL to about 4 µg/mL, from about 1 µg/mL to about 3 µg/mL, from about 2 µg/mL to about 5 µg/mL, from about 3 µg/mL to about 5 µg/mL).

In some embodiments, the buffer condition has a pH from about 10 to about 12 (e.g., from about 10.5 to about 12, from about 10.5 to about 11.5, from about 10 to about 11.5, from about 10 to about 11).

The sample may be any suitable sample, including industrial from a biofuel fermentation process, for example, for producing biofuel that includes ethanol and/or butanol. The sample may include debris such as that of corn mash and/or sugar cane.

In certain embodiments, the yeast is the species of *Saccharomyces cerevisiae*.

In another aspect, the invention generally relates to a method for determining yeast viability. The method includes: staining a sample to be tested for yeast viability with a first dye and with a second dye under a buffer condition having a pH of about 10 to about 12.5; acquiring a fluorescent image of the first dye-stained sample; acquiring a fluorescent image of the second dye-stained sample; and comparing the fluorescent image of the first dye-stained sample and the fluorescent image of the second dye-stained sample to determine yeast viability.

For example, the first dye may be selected from the group consisting of Acridine Orange, SYTO 9, DAPI, Hescht, Calcofluor White and the second dye is selected from the group consisting of Propidium Iodide, Ethidium Bromide, Oxonol, Mg-ANS.

In certain embodiments, the first dye is Acridine Orange and the second dye is Propidium Iodide. For example, Acridine Orange may be at a concentration from about 1 µg/mL to about 5 µg/mL (e.g., from about 1 µg/mL to about 4 µg/mL, from about 1 µg/mL to about 3 µg/mL, from about 2 µg/mL to about 5 µg/mL, from about 3 µg/mL to about 5 µg/mL). Propidium Iodide is at a concentration from about 1 µg/mL to about 5 µg/mL (e.g., from about 1 µg/mL to about 4 µg/mL, from about 1 µg/mL to about 3 µg/mL, from about 2 µg/mL to about 5 µg/mL, from about 3 µg/mL to about 5 µg/mL).

In yet another aspect, the invention relates to a method for determining the concentration of viable yeast cells. The method includes: staining a sample to be tested with a first dye and with a second dye under a buffer condition having a pH of about 10 to about 12.5; acquiring at least one static fluorescent image of the first dye-stained sample; acquiring at least one static fluorescent image of the second dye-stained sample; and analyzing the at least one static fluorescent image of the first dye-stained sample and the at least one static fluorescent image of the second dye-stained sample to determine the concentration of viable yeast cells in the sample.

In yet another aspect, the invention generally relates to a method for determining yeast viability. The method includes: staining a sample to be tested for yeast viability with a first dye and with a second dye under a buffer condition having a pH of about 10 to about 12.5; acquiring at least one static bright-field image and at least one static fluorescent image of the first dye-stained sample; comparing the at least one bright-field image to the at least one fluorescent image of the first dye-stained sample to determine a characteristic of viable yeast cells in the sample; acquiring at least one static bright-field image and at least one static fluorescent image of the second dye-stained sample; and comparing the at least one bright-field image to the at least one fluorescent image of the second dye-stained sample to determine a characteristic of non-viable yeast cells in the sample. The method may further include determining the concentration of viable yeast cells.

In yet another aspect, the invention generally relates to a method for determining the concentration of viable yeast cells. The method includes: staining a sample to be tested with a first dye and with a second dye under a buffer condition having a pH of about 10 to about 12.5; acquiring at least one static bright-field image and at least one static fluorescent image of the first dye-stained sample; acquiring at least one static bright-field image and at least one static fluorescent image of the second dye-stained sample; and determine the concentration of viable yeast cells in the sample.

In yet another aspect, the invention generally relates to a method for determining yeast viability. The method includes: staining a sample to be tested for yeast viability with Acridine Orange under a buffer condition of pH of about 10.5 to about 12.5; acquiring at least one static bright-field image of the Acridine Orange-stained sample by directing a bright-field light beam to the sample; acquiring at least one static fluorescent image of the Acridine Orange-stained sample by directing an excitation light beam to the sample; comparing the at least one bright-field image to the at least one fluorescent image of the Acridine Orange-stained sample to determine the characteristics of the viable yeast in the sample; staining a sample to be tested for yeast viability with Propidium Iodide under a buffer condition of pH of about 10.5 to about 12.5; acquiring at least one static bright-field image of the Propidium Iodide-stained sample by directing a bright-field light beam to the sample; acquiring at least one static fluorescent image of the Propidium Iodide-stained sample by directing an excitation light beam to the sample; comparing the at least one bright-field image to the at least one fluorescent image of the Propidium Iodide-stained sample to determine the characteristic of the non-viable yeast in the sample; and determining the yeast viability of the sample.

EXAMPLES

Fluorescent Stain Selection

To optimize an assay protocol for yeast viability measurement, fluorescent stains that are selected to determine live or dead cells should be bright and have low background signals. Eight different fluorescent stains were compared using Cellometer Vision with the excitation/emission pairs of 375 nm/450 nm, 470 nm/525 nm, and 527 nm/595 nm. The dyes were performed on Munton dehydrated yeasts diluted to approximately $2 \times 10^6$ particles/mL. Acridine orange (AO), SYTO 9, DAPI, Hoescht, Calcofluor white are total cell staining agents, and Mg-ANS, propidium iodide (PI), ethidium bromide (EB) are viability dyes that can enter cells with compromised membrane. A concentration series was performed for each dye to observe the approximated optimal concentration and analyze the signal-background-ratio.

The dyes that are excited by ultraviolet (375 nm) light are DAPI, Hoescht, calcofluor white, and Mg-ANS. DAPI, Hoescht, and calcofluor white stain all cells, but due to the biological structure of yeasts that contains an inner membrane and an outer cell wall, making the staining unpredictable. The results, shown in FIG. 1, for UV dyes showed non-uniform fluorescence of yeast cells. For Mg-ANS, a viability dye, it stains only the dead yeast cells, which had a uniform fluorescence signal at lower concentrations. Overall, ultraviolet dyes have high auto-fluorescence background from the substrate, and the availability of low-power, high-brightness UV LED is uncommon.

Figure 2:
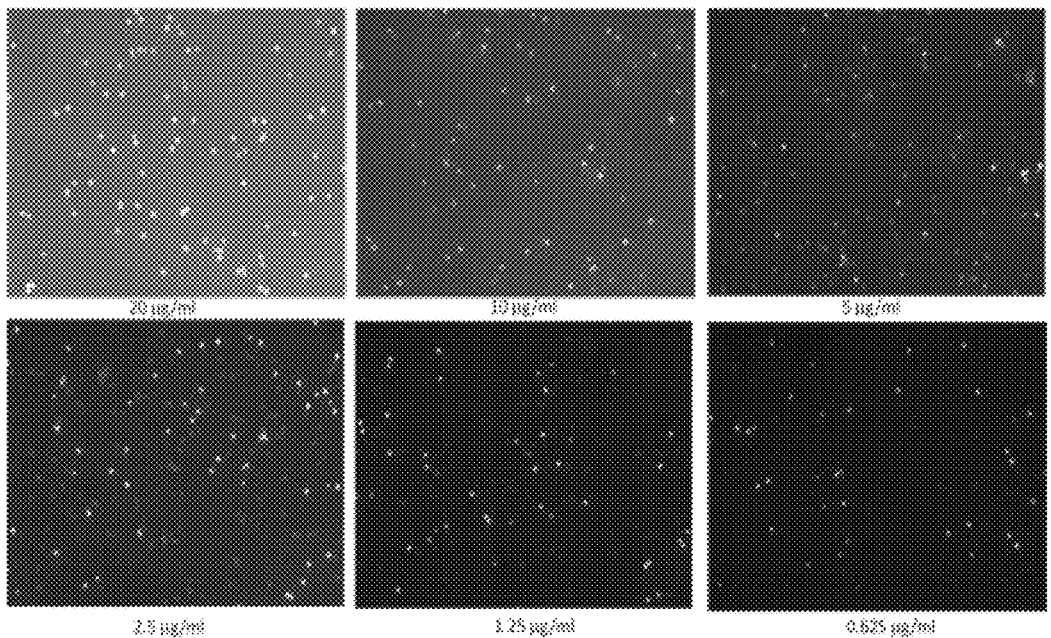
FIG. 2 depicts 2 blue excited dyes at various concentrations, where fluorescence signals of yeasts are compared.
Figure 2:
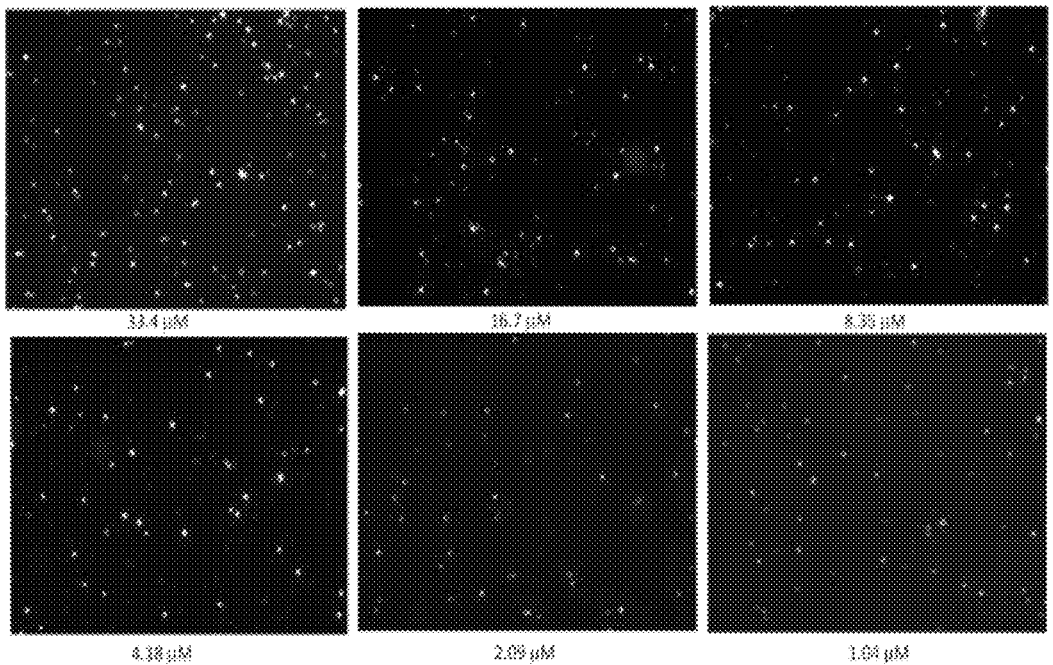

The dyes excited by blue (470 nm) light are Acridine Orange and SYTO 9, where both dyes stain total cells, but similar to the UV dyes, it generates non-uniform fluorescence. At lower concentration of both dyes some yeast cells are brightly stained than others, which correspond to the membrane compromised cells. (FIG. 2)

Figure 3:
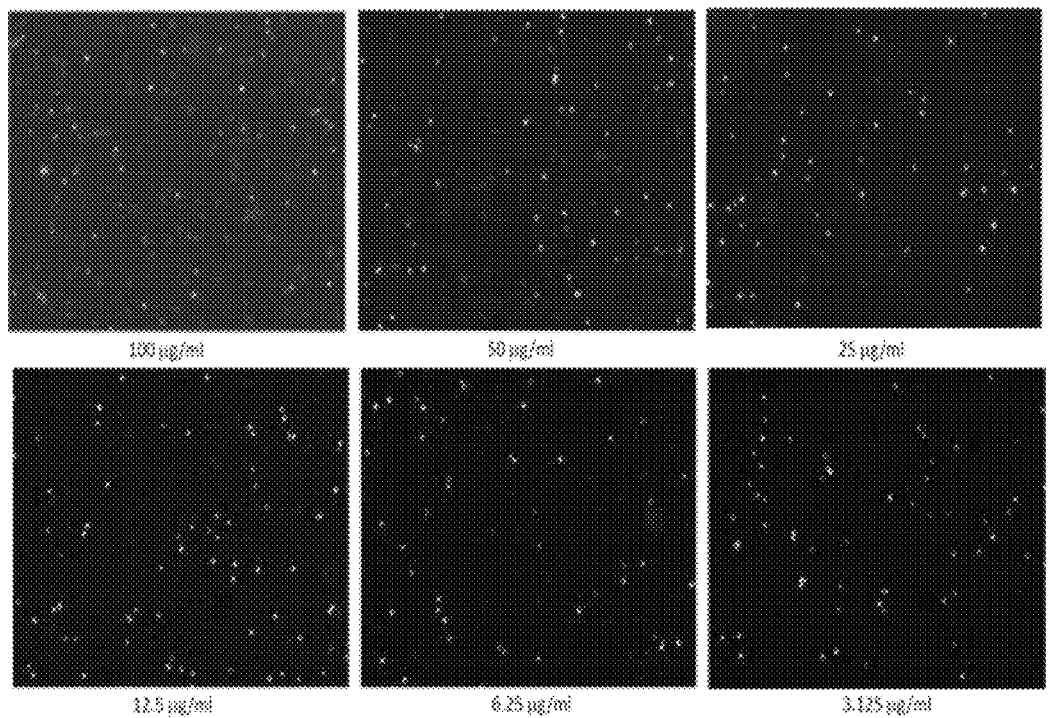
FIG. 3 depicts 2 green excited dyes at various concentrations, where fluorescence signals of yeasts are compared.
Figure 3:
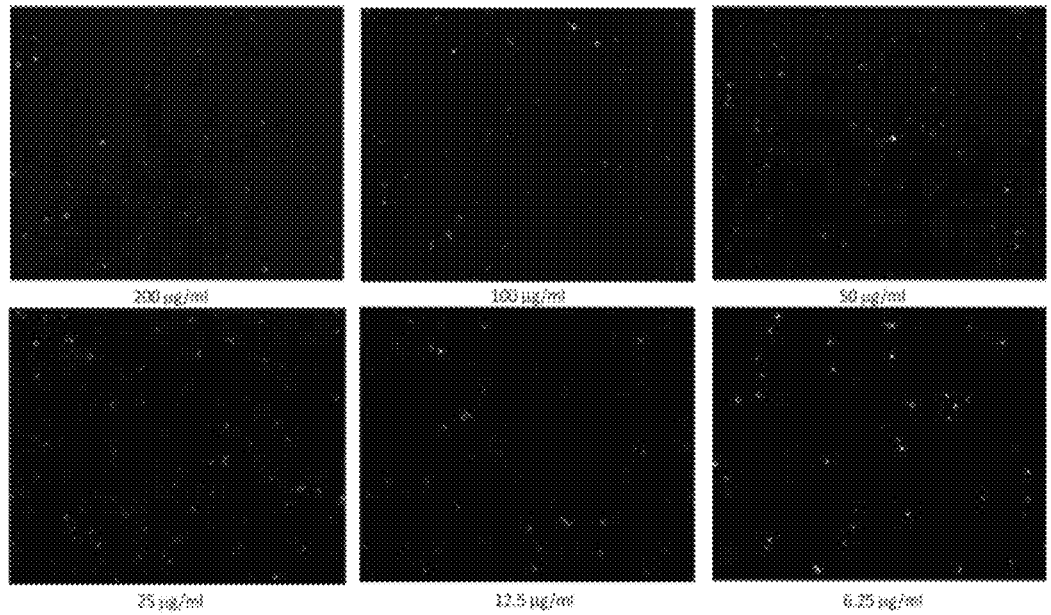

The dyes that are excited by green (527 nm) light are ethidium bromide and propidium iodide, which are viability stains for dead cells. At high concentration, background fluorescence is induced in every cell. As the concentration decreases, the dead cells signals increased (FIG. 3). PI has much lower background fluorescence than EB.

Overall, AO, SYTO 9 are more suitable for total cell stain and PI is more suitable for dead cell staining. Therefore, these three dyes were further explored for optimization for messy sample.

Optimization of pH Level

Figure 4:
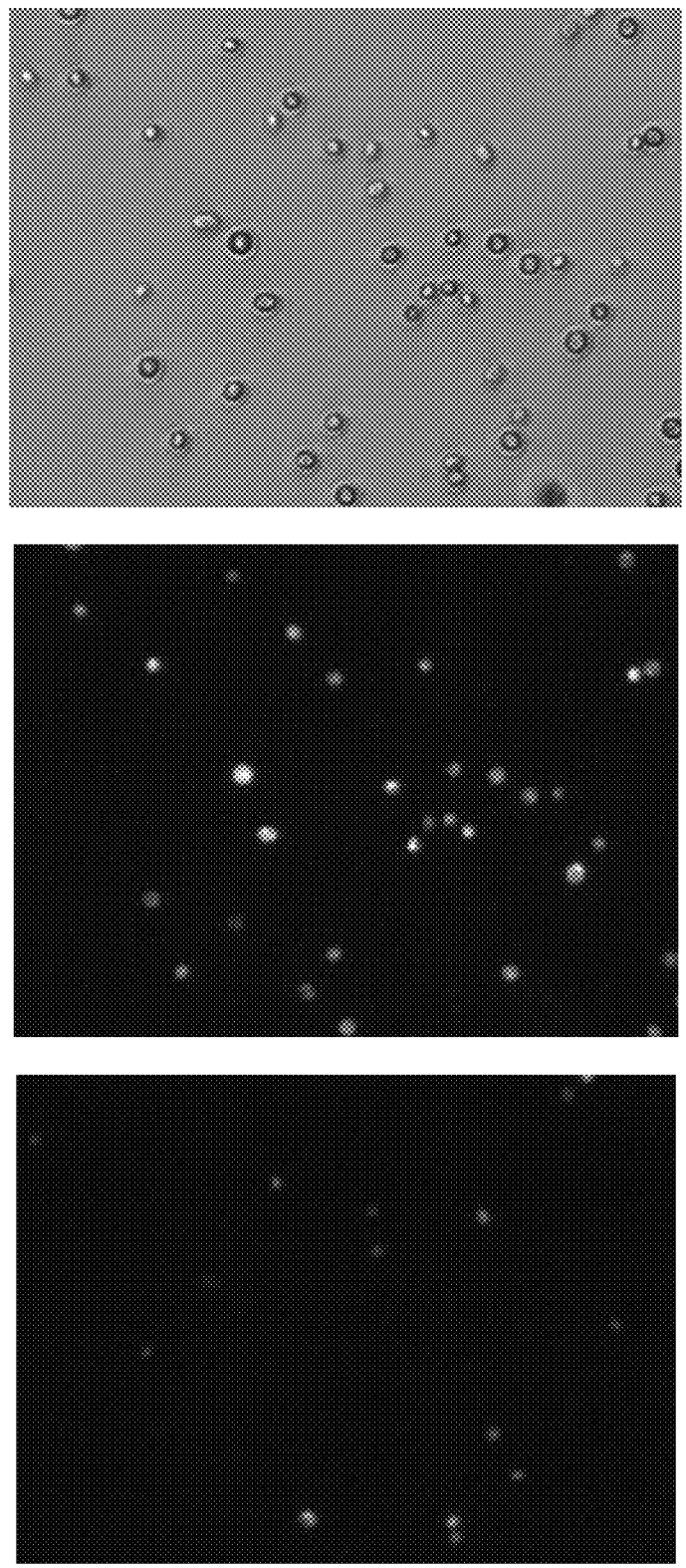
FIG. 4 depicts an example of bright-field image (left), viable yeasts (right), and nonviable yeasts (bottom) using SYTO 9 (viable) and Propidium Iodide (nonviable) stains on pure yeast sample.

Previously, SYTO 9 and PI have been used to determine viability of yeasts (Invitrogen), and by using Cellometer Vision, consistent results can be obtained. The optimal concentrations for SYTO 9 and PI are approximately 3 µM and 41 µg/mL, respectively. (FIG. 4)

Figure 5:
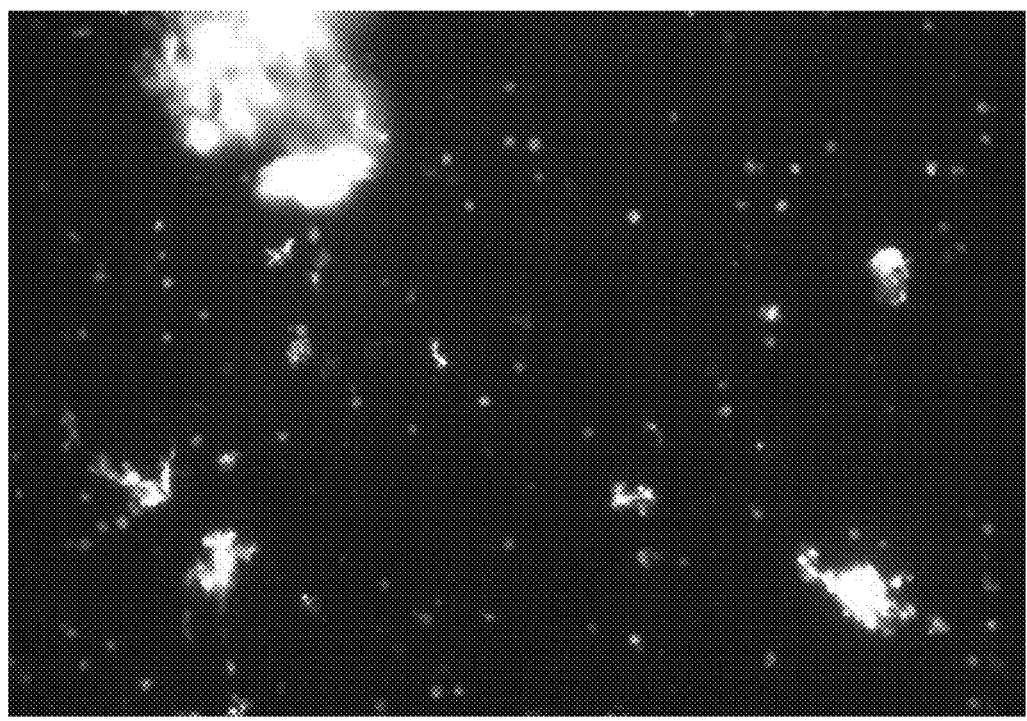
FIG. 5 depicts an example of a fluorescent image of live cell stain of either Acridine Orange or SYTO 9 with yeasts in corn mash samples, where a large nonspecific fluorescent signal is shown from the corn mash debris.

SYTO 9 and PI worked very well with dehydrated yeasts, but when tested with yeasts in corn mash, both AO and SYTO 9 did not stain the live cells very well. In addition, large fluorescent background is shown, as shown in FIG. 5, where the debris light up brightly, making automatic counting impossible.

Figure 6:
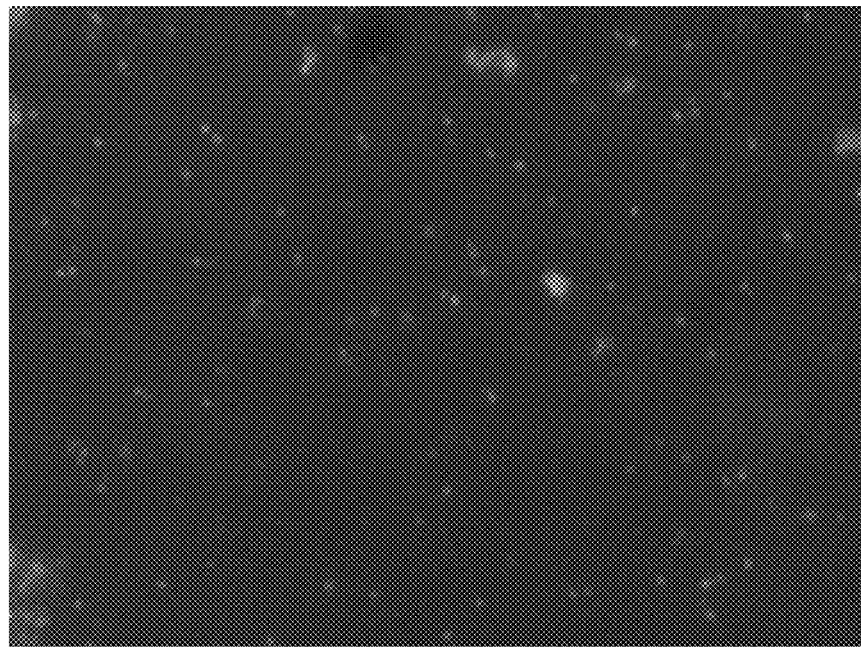
FIG. 6 depicts a series of yeast in corn mash fluorescent images from pH 7-pH 9, where the corn mash still shows nonspecific signals.
Figure 6:
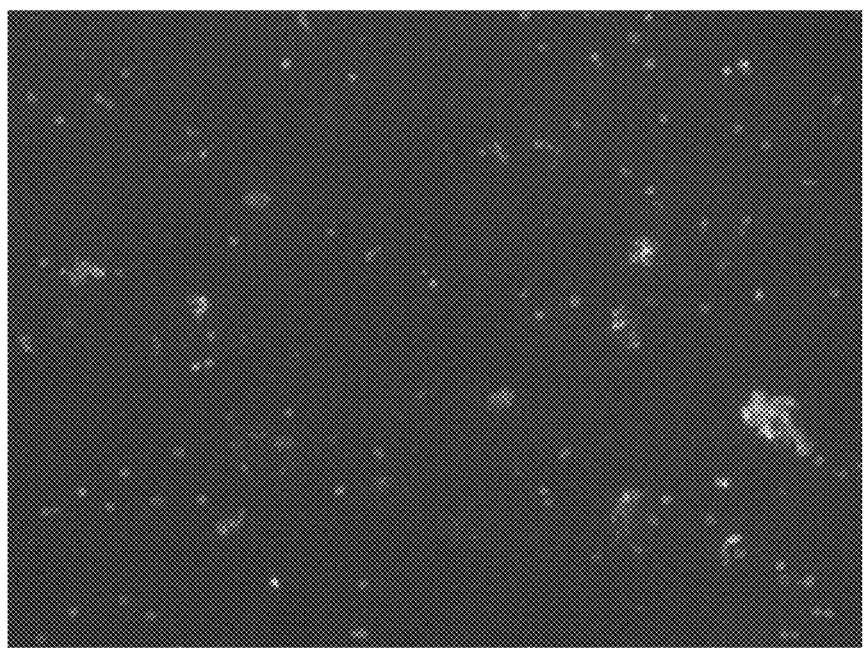
Figure 6:
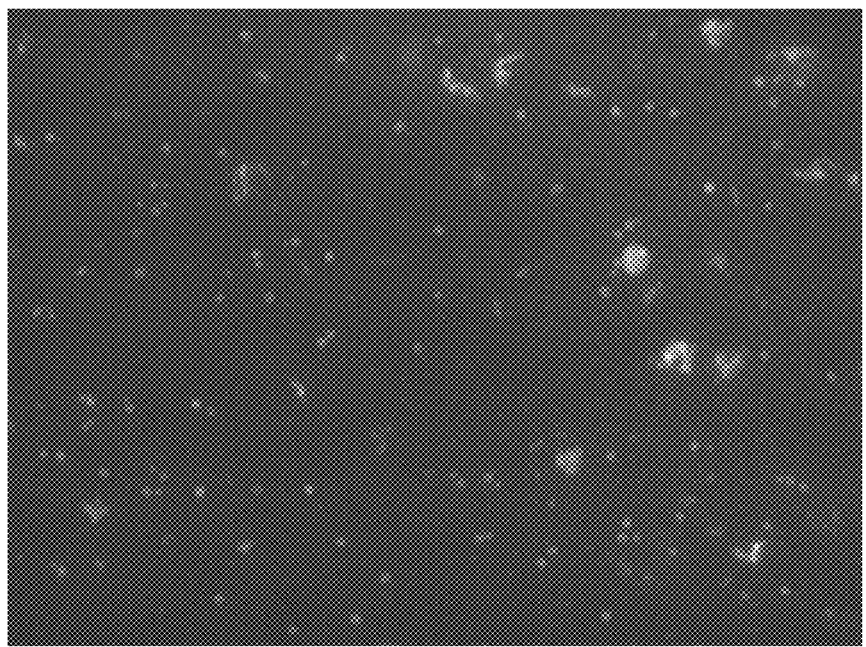
Figure 6:
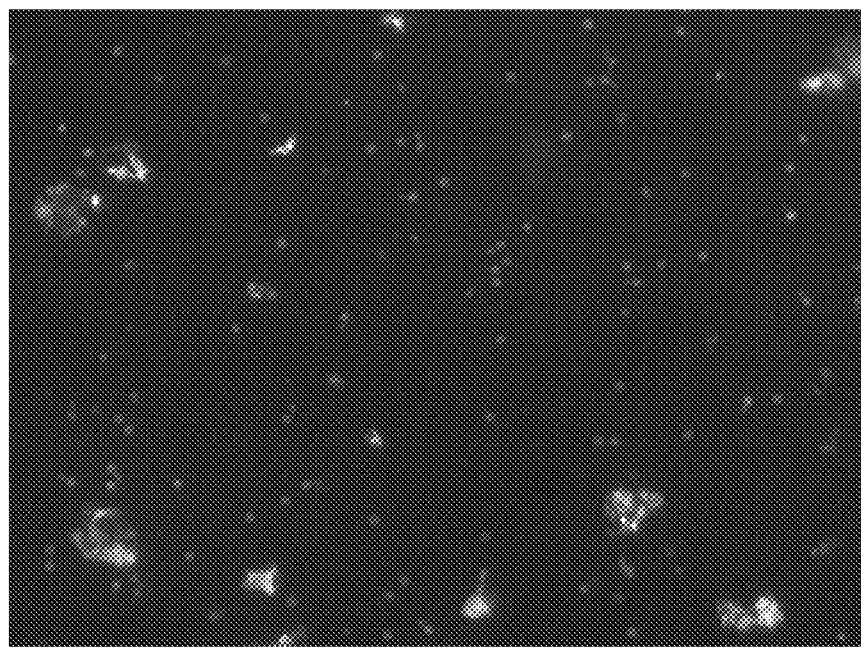
Figure 7:
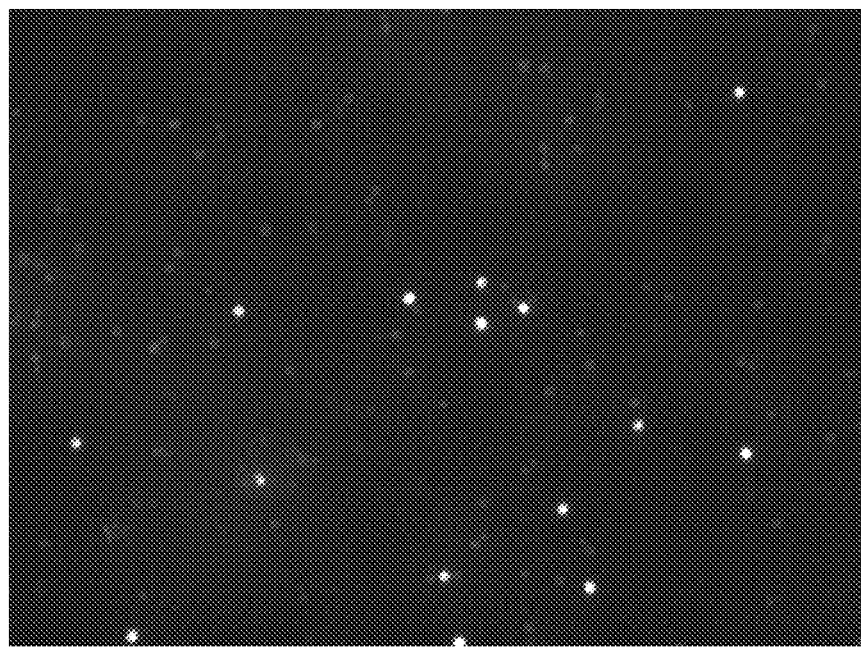
FIG. 7 depicts a series of yeast in corn mash fluorescent images from pH 10-pH 11.50, where the nonspecific signals of corn mash are removed.
Figure 7:
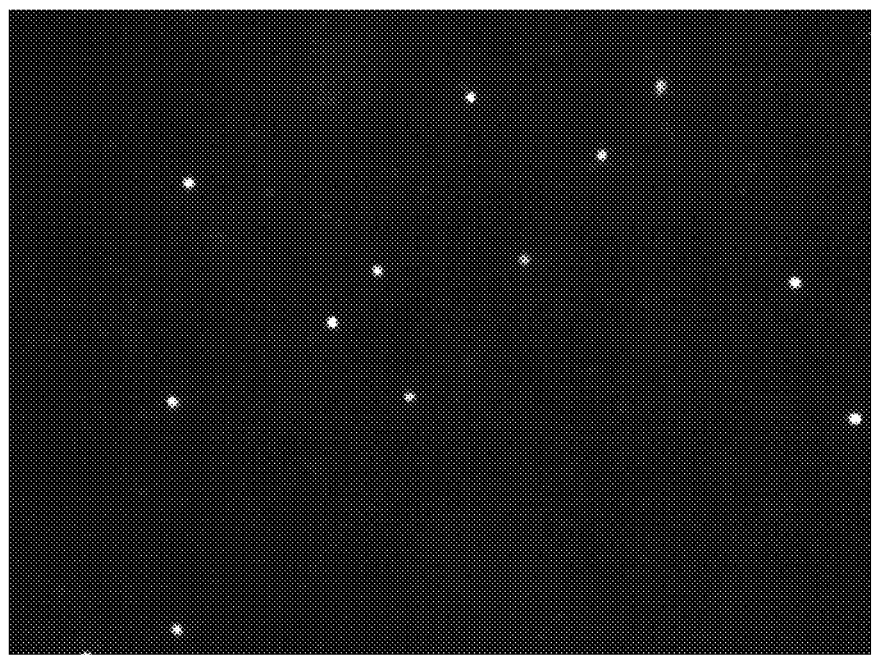
Figure 7:
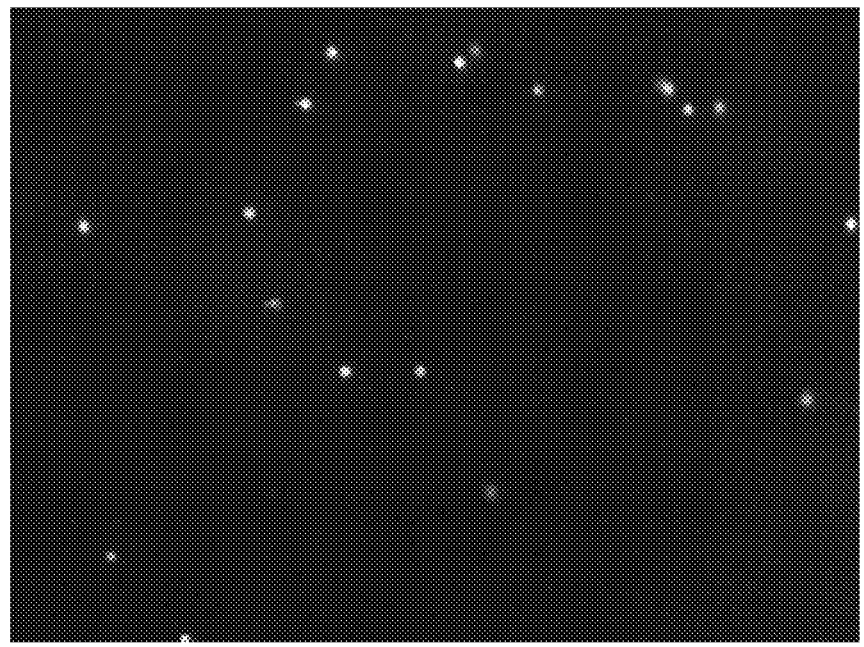
Figure 7:

In general, fluorescent signal yielded by AO was much better than SYTO 9, thus a pH series experiment will be performed (FIG. 6 and FIG. 7). The results showed that at pH greater than 8, the background fluorescence of debris are eliminated (similar to honey bee spores) and the live cells are stained brightly.

Concentration Optimization of AO and PI Mixture

Figure 8:
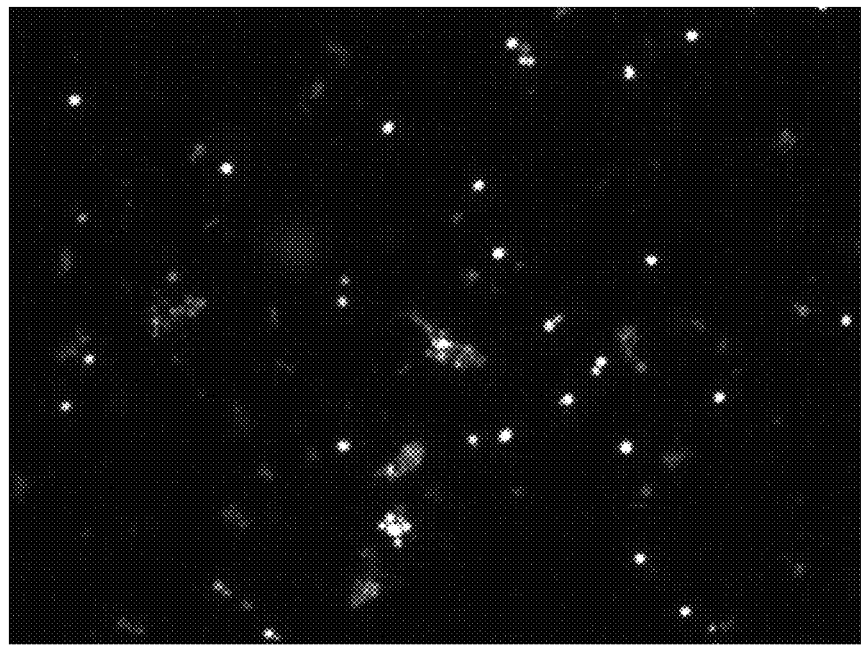
FIG. 8 depicts a series of concentration adjustment at high pH level for Propidium Iodide, which also eliminated the corn mash signals.
Figure 8:
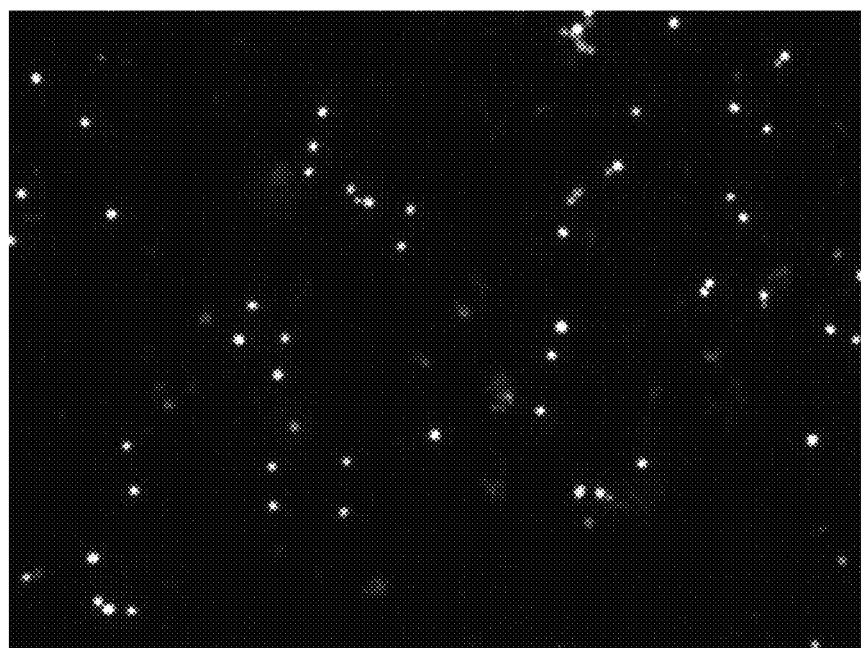
Figure 8:
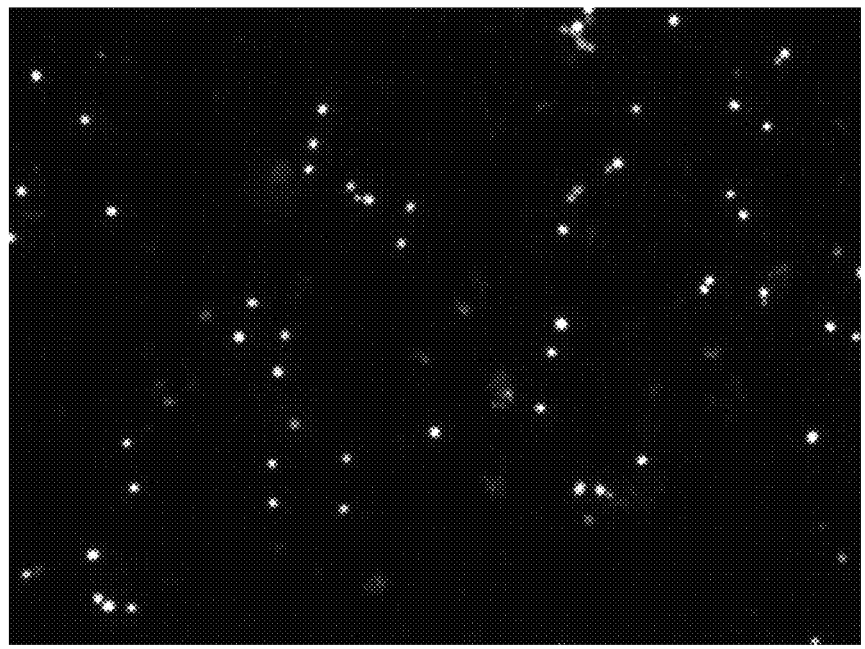
Figure 8:
Figure 8:
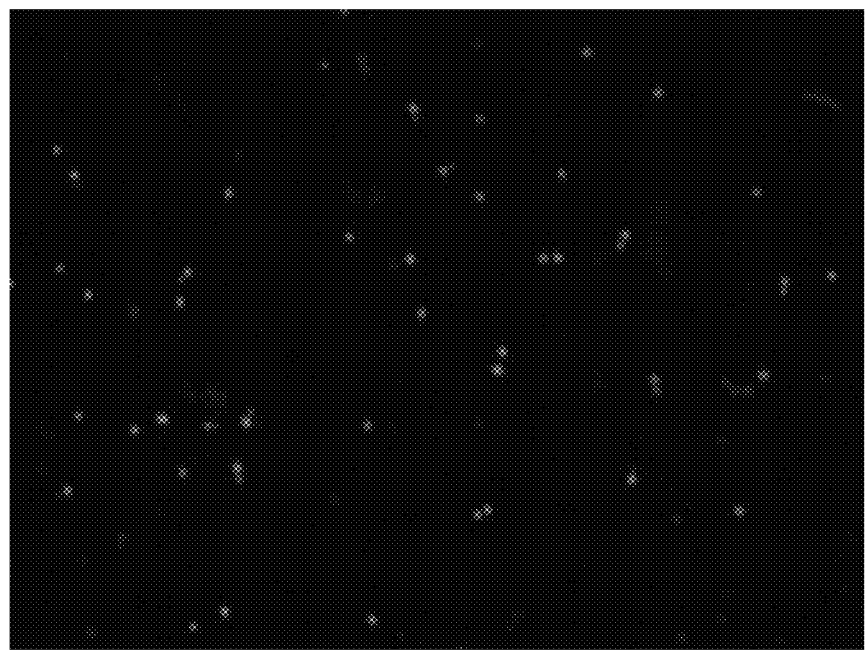

The AO staining of live cells can be adjusted by optimizing the pH level of the buffer, but at the same time, PI concentration has to be also compensated to quench AO fluorescence in dead cells. In addition, PI would stain the debris as well, thus the concentration can be adjusted to reduce the debris signals. (FIG. 8)

Measurement of Fermentation Samples

Figure 9:
FIG. 9 depicts 2 examples of real fermentation yeast samples from operating fermenters, using the discovered fluorescence detection method to clearly distinguish between viable and nonviable yeasts in corn mash.
Figure 9:
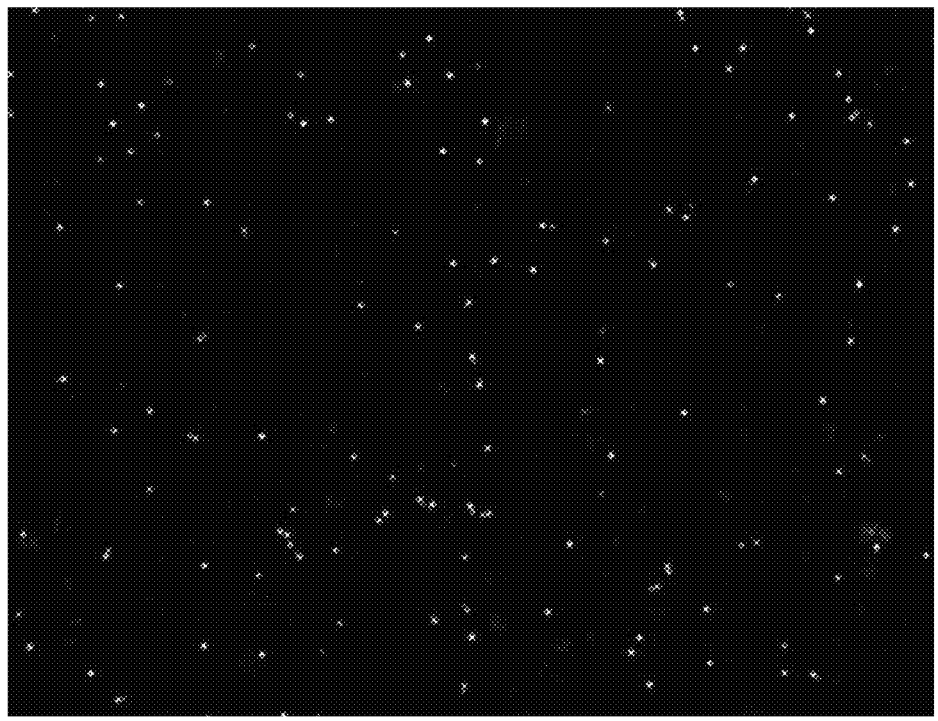
Figure 9:
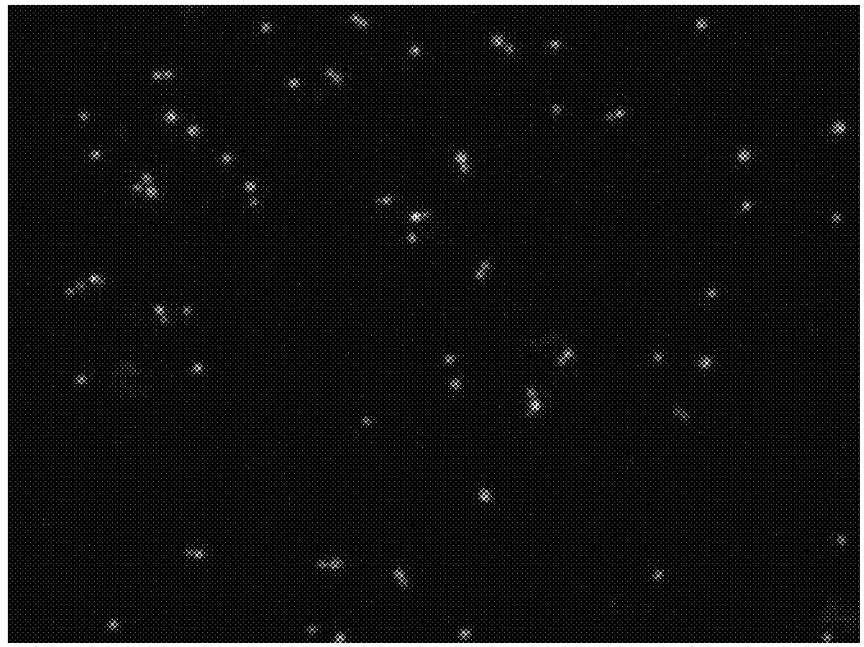
Figure 9:
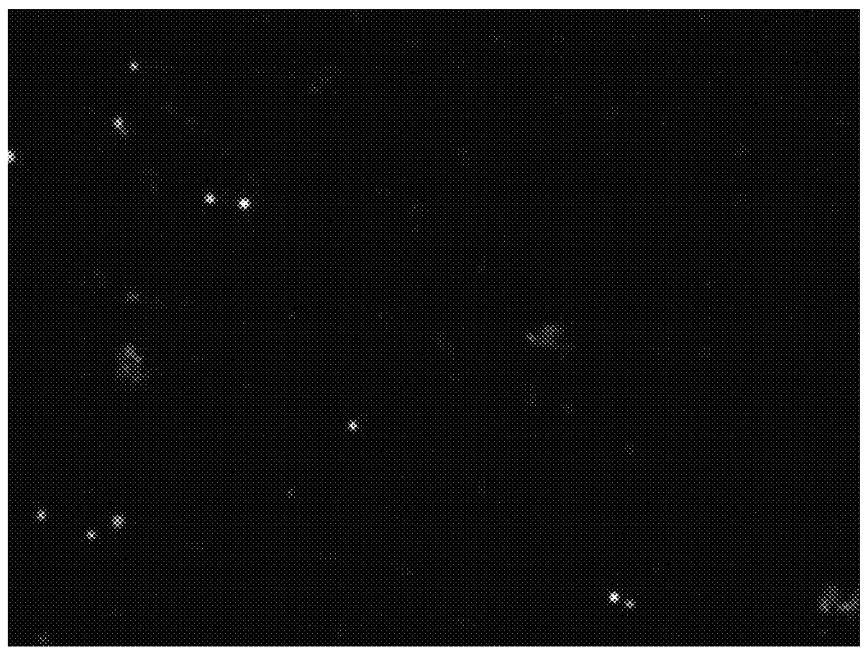

The AOPI mixture at adjusted pH was tested on several fermentation stages of yeasts in corn mash. Numerous counting were tested with Fermentation 2 to check the consistency of the protocol. First 10 µL of fermentation sample is mixed with 5 µL of AO and PI each at 5 µg/mL, and finally the pH was adjusted with 5 µL of 0.05 M NaOH. More than 11 trials were conducted on Fermentation 2, an average of 19.24%+/−2.35% viability was calculated. In addition, yeast samples were pre-diluted with adjusted pH, and then it was mixed 1:1 with 10 to 10 µL of samples and AOPI stain for one min. After incubation for one min, the solution is pipetted into low FL background slide and insert into Cellometer Vision. Over a period of 2-3 min, the background debris fluorescence diffused out leaving only bright live cells in the AO channel, while the low PI concentration will brightly stain the dead cells leaving the debris also unstained. (FIG. 9)

Buffer Selection

Figure 10:
FIG. 10 depicts 2 examples of real fermentation yeast samples from operating fermenters, using the discovered fluorescence detection method to clearly distinguish between viable and nonviable yeasts in corn mash.
Figure 10:
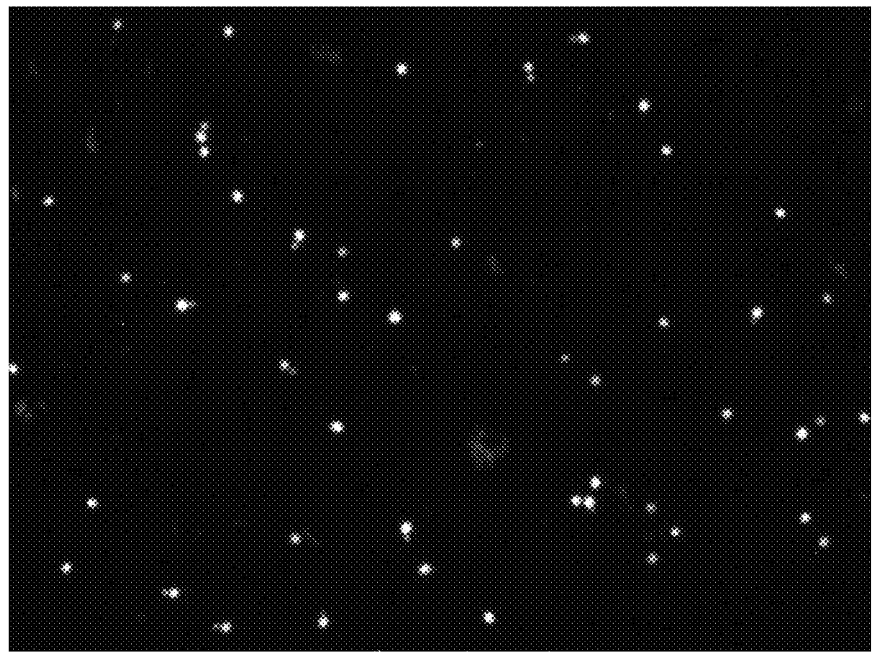
Figure 10:
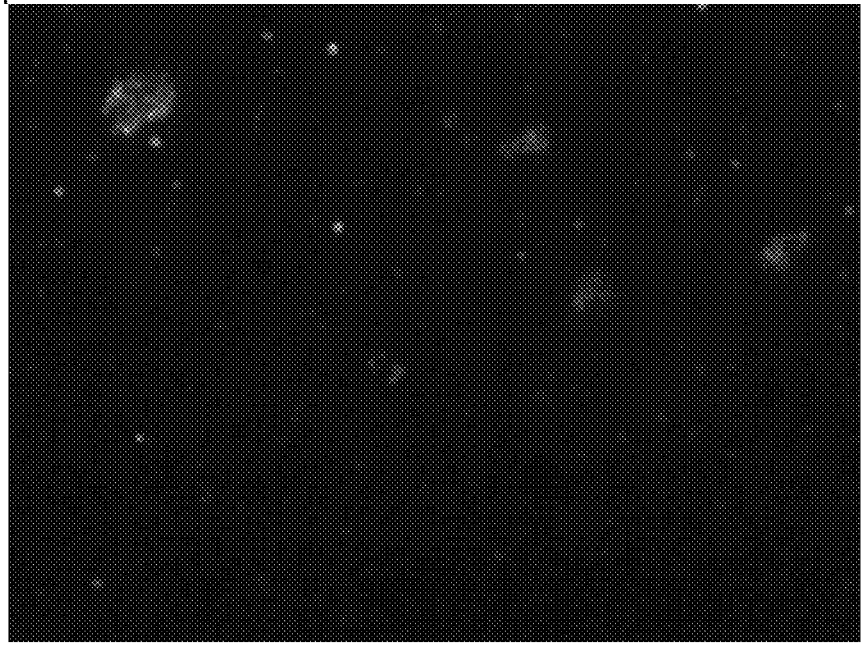
Figure 10:
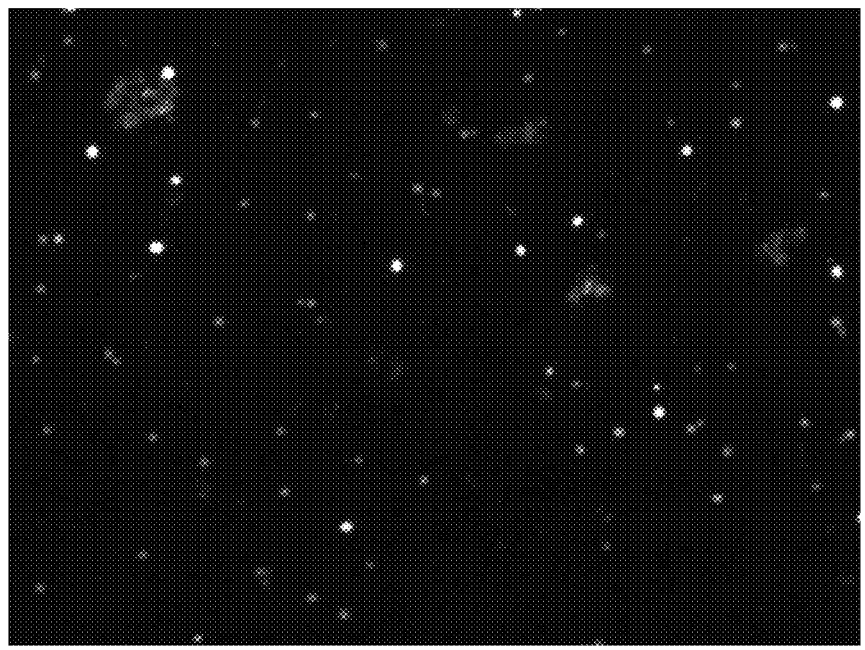

Certain experiments were performed by directly changing the pH of the yeast sample and stain to ~10 by using NaOH, but it is necessary to select a stable buffer at an optimal pH level and ionic strength for consistent fluorescence detection and concentration measurement. A Trizma base and a Trizma 8.8 were selected to test the capability to stain the yeasts without minimum background. (FIG. 10)

The Trizma Base yields a buffer at pH~10 and was diluted in water to 0.1 M, which resulted in a clean background for both AO and PI channel. However, the Trizma 8.8 was not high enough to minimize the background and also enhance the yeast signals. The background signals of debris are still observable and also the dead yeasts in the AO channel, which creates some confusion between live and dead cells.

Characterization of Yeast in Corn Mash

The yeast and corn mash mixtures provided are initially characterized by measuring the pH level and ethanol content of each sample. The average pH level for sample 1-7 is 4.45+/−0.18 and the ethanol contents are progressively increasing from 1.8% to 14.7% respectively. Since the pH tolerance of yeasts is high, the low pH level in each sample can prevent bacterial contamination. In general, during a fermentation process, as ethanol percentage increases in the fermenter, the viability of yeasts decreases, which ultimately terminates the production of bioethanol. Therefore, if one could easily monitor the viability of yeasts in the different fermentation stages, when attempting to prolong the life-cycle of yeasts, higher final ethanol output may be achieved.

The dilution buffer of the invention is compared to cell culture grade $H_2O$ and PBS to obtain the highest fluorescence signal as well as low background level. FIG. 12a showed the signal-to-background ratio of the yeasts for both AO and PI. For PI staining, all three solutions showed comparable signal-to-background ratio for nonviable cells, but the nonspecific fluorescence of corn mash debris is higher for $H_2O$ and PBS. The AO fluorescence has the largest differences between the dilution buffers, where the $H_2O$ and PBS did not show any fluorescent signal for viable cells. In contrast, yeasts diluted in the buffer disclosed herein displayed strong AO fluorescence and minimal signals for the nonviable cells, which confirms the fluorescence resonance energy transfer of AO to PI.

The result of the concentration series is shown in FIG. 12b, where high signal-to-background ratios are shown for both AO and PI at each concentration. The nonspecific fluorescence from the debris and background fluorescence are also compared. As the concentration of both dyes decreases, the nonspecific fluorescence from the corn mash debris also decreases. The optimized concentration is approximately 1.25 µg/mL for both AO and PI due to the fact that it showed high signal-to-background ratio as well as low nonspecific fluorescence signals. By increasing or decreasing the concentration ratio of AO:PI would alter the fluorescent response from the yeasts (data not shown). If the AO concentration is higher than PI, the AO would fluoresce brighter along with the increase in the debris nonspecific signals. More importantly, PI is not sufficient in quenching the AO signals from nonviable cells, which lead to poor distinction between live and dead yeasts. However, if AO concentration exceeds 20 µg/mL, then self-quenching of AO molecules may occur due to the formation of dimers, which inhibits its own fluorescence. On the other hand, if AO concentration is lower than PI, the AO signal would be weaker, but offered good distinction between live and dead yeasts. Therefore, by keeping AO and PI at the same concentration eliminates the issues of unbalanced AOPI mixture.

Figure 13:
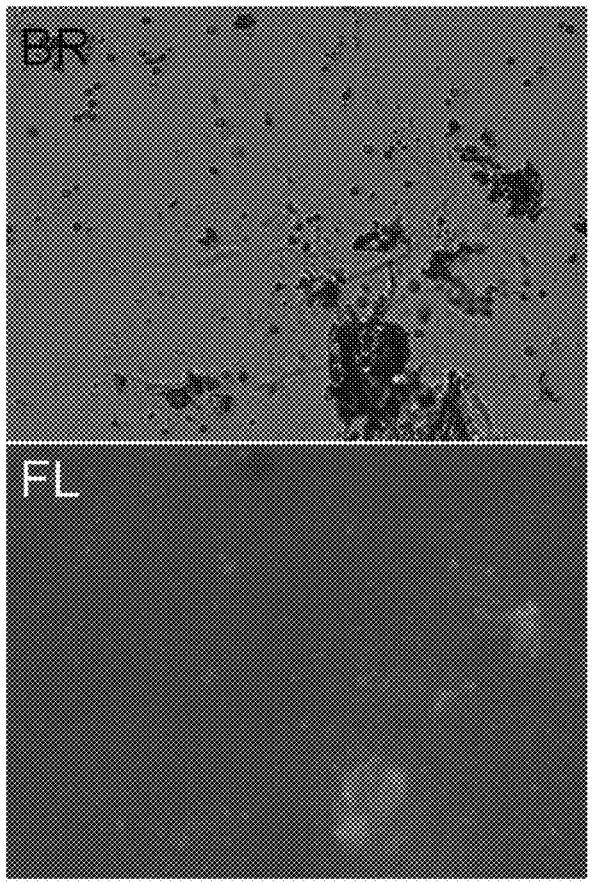
FIG. 13 depicts an example of nonspecific and weak fluorescence signal of Acridine Orange, and an example of nonspecific signal of Propidium Iodide of yeast in corn mash samples.
Figure 13:
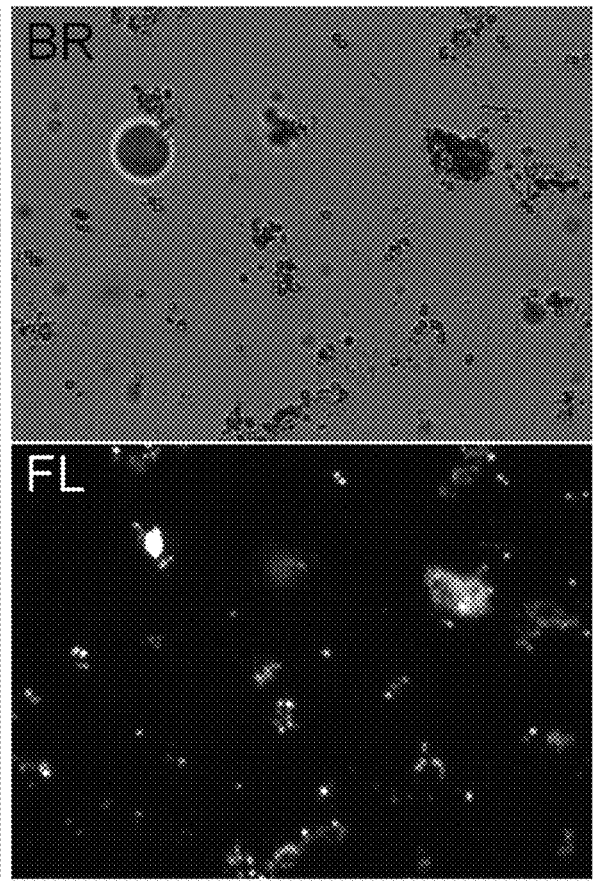

Using the buffer selected and optimized dye concentrations, the concentration and viability of each yeast sample are measured by the Cellometer imaging cytometry method. Examples of the bright-field and fluorescent images of the seven yeast samples are shown in FIG. 13. Each fluorescent image is a combination of the fluorescence signals from AO and PI channels with pseudo colors green and orange, respectively. The counted yeast cells are circled by the software, which clearly distinguished the viable cells, nonviable cells, and debris. The yeast cells were effectively stained with high fluorescence intensities, while the corn mash nonspecific signals are minimized. The average total cell concentrations calculated for sample 1-7 are 0.41, 1.33, 1.20, 0.94, 1.31, 1.32, and $0.97 \times 10^8$ particles/mL, while the average viability measurements are 83.8%, 90.4%, 94.0%, 75.9%, 80.8%, 60.9%, and 24.1% respectively. The average total cell concentrations using manual hemocytometry for sample 1-7 are 0.54, 1.43, 1.31, 0.78, 1.18, 1.14, $0.85 \times 10^8$ particles/mL and the average viability measurements are 80.0%, 90.7%, 85.9%, 72.3%, 80.5%, 60.3%, and 19.5% respectively (FIG. 13).

Although two of the samples (1 and 4) showed lower cell concentrations due to inadequate pipetting of the thick mixtures, the results obtained from both Cellometer and hemacytometer were consistent. Excluding samples 1 and 4, the other samples exhibited an average of $1.18 \times 10^8$ and $1.22 \times 10^8$ particles/mL for Cellometer and hemacytometer, respectively, which shows the consistency of the novel imaging cytometry method between samples. Since the initial yeast and corn mash samples were diluted 1:20 (v/v) with the dilution buffer, the counting results obtained are multiplied by a factor of 20 automatically.

Figure 14:
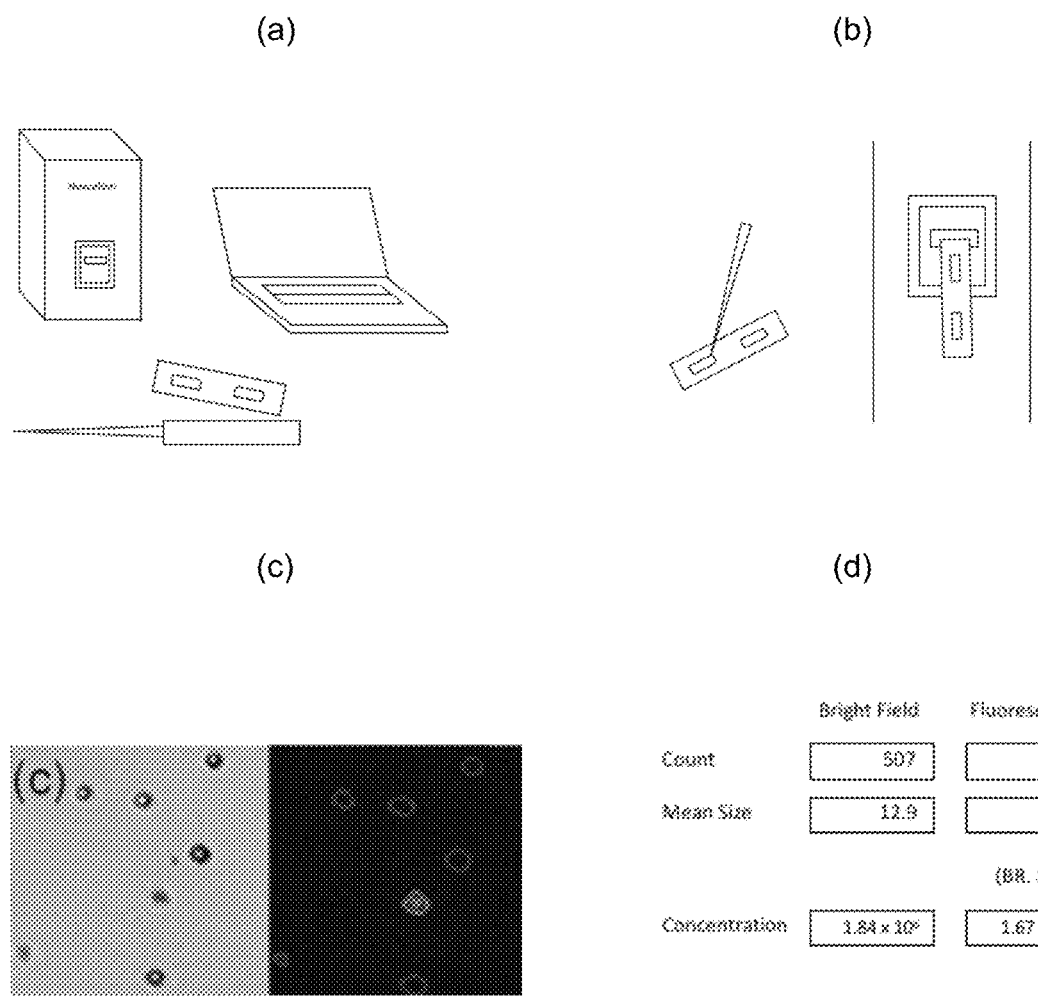
FIG. 14 depicts a figure of the Cellometer® (Nexcelom Bioscience) used primarily in conjunction with the invention to measure viability of yeasts in corn mash.
Figure 15:
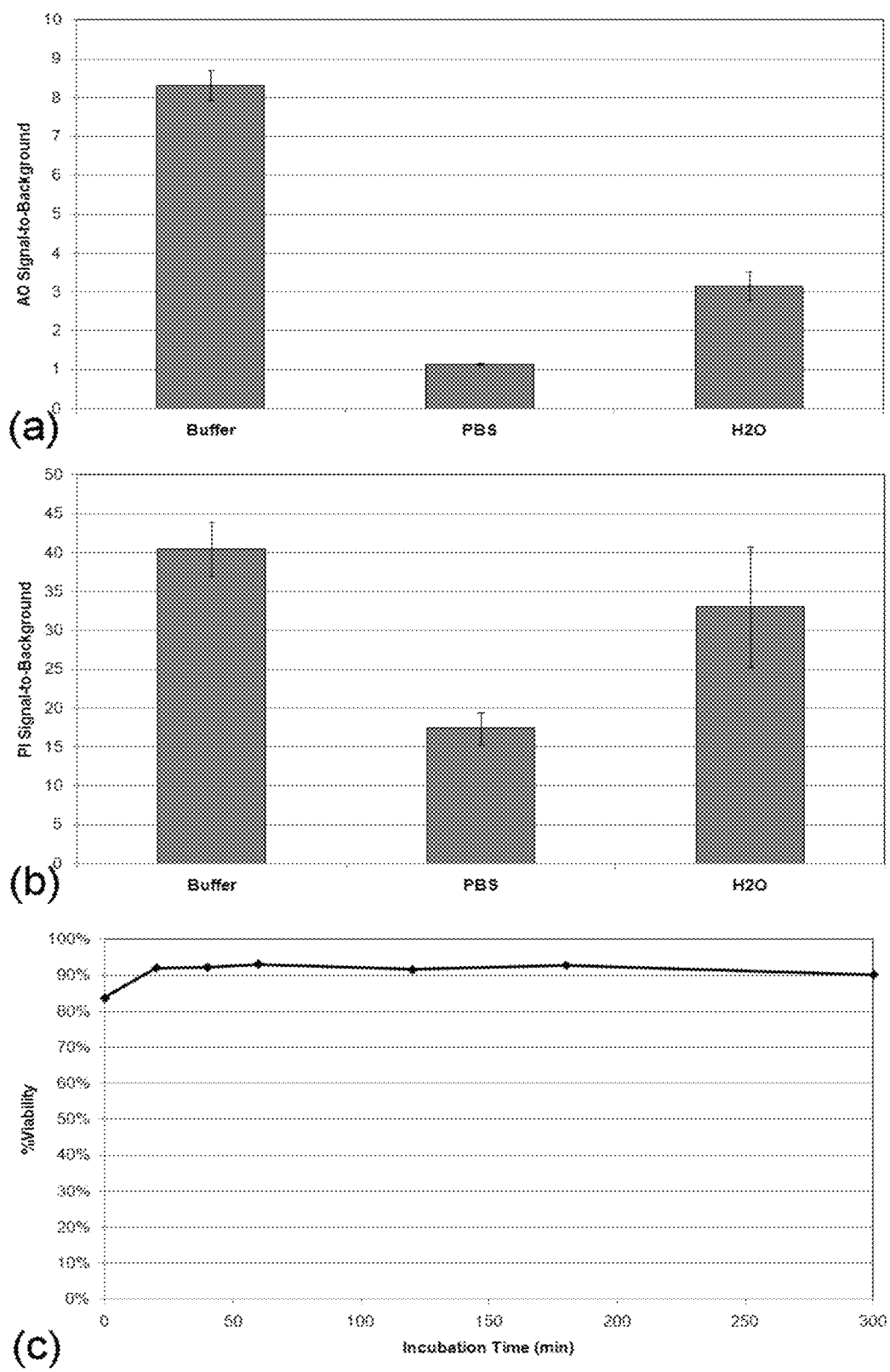
FIG. 15 depicts plots of signal-to-background ratio of (a) Acridine Orange and (b) Propidium Iodide in respect to different buffers. The method is stable for over 5 hours of incubation period (c).
Figure 16:
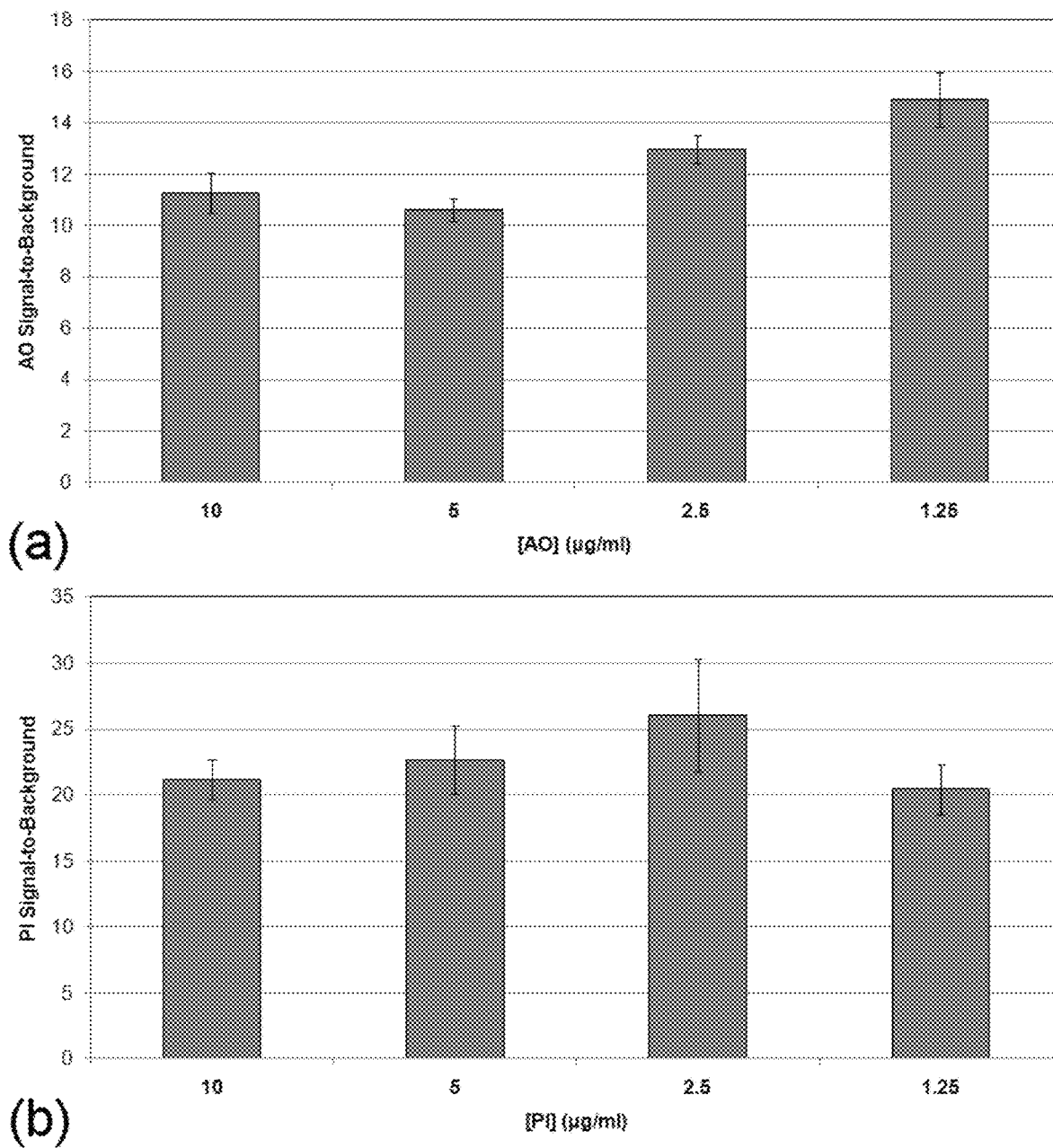
FIG. 16 depicts plots of signal-to-background ratio of (a) Acridine Orange and (b) Propidium Iodide in respect to different concentrations.

The pipetting error for concentration measurements does not affect the viability measurement in this experiment because the cell count ratios of viable and nonviable cells are properly measured. There is a general trend of viability reduction due to the increase in ethanol percentage, which is plotted in FIG. 14. In this experiment, the Cellometer was able to verify the decrease in viability during the entire fermentation process. The control sample that was diluted in cell culture grade $H_2O$ showed poor imaging results due to weak live cell fluorescence signal and nonspecific fluorescent signals from corn mash (FIG. 15).

Utilizing the combination of Cellometer® Vision and the dilution buffer of the invention to directly measure yeast concentration and viability from fermenters is of great significance for the biofuel industries in the United States. Accurately measuring viabilities of yeasts in fermenters would allow biofuel factories to produce consistent bioethanol output. Furthermore, it would facilitate the consistency between fermenters and increase efficiency of the ethanol production. Another advantage is the reduction of time spent on manual cell counting, where by using the imaging cytometry counting method, trained technicians can easily setup and run multiple samples in less than 10 min. In general, the yeast concentration is counted only in the first 2-3 h of the fermentation process. The efficiency and effectiveness of this novel imaging cytometry method can be easily incorporated to monitor yeast viability throughout the entire fermentation process.

The Cellometer® Vision has demonstrated accurate and consistent pure yeast concentration and viability measurement previously (http://www.nexcelom.com/Applications/Yeast-Viability.html), for example, the capability of measuring yeast concentration and viability in corn mash, where strong fluorescence signals from detected and counted from viable and nonviable yeast cells, while nonspecific staining of corn mash is minimized to facilitate effective automated cell counting algorithm. The development of the counting assay using Cellometer® Vision and the diluting buffer in conjunction provides a novel method for biofuel industries in the United States to consistently and accurately monitor yeast viability during fermentation process to ensure quality bioethanol output. Furthermore, the incorporation of this novel imaging cytometry method in biofuel plants can support research for enhancing bioethanol production, which will be a critical development as fossil reduction and global warming issues increase. (Pretorius, et al., "Designer Yeasts for the Fermentation Industry of the $21^{st}$ Century," *Food Technology Biotechnology*, vol. 41, pp. 3-10, 2003; Graves, et al., "Effect of pH and lactic or acetic acid on ethanol productivity by *Saccharomyces cerevisiae* in corn mash," *Journal of Industrial Microbiology and Biotechnology*, vol. 33, pp. 469-474, 2006; Graves, et al., "Interaction effects of lactic acid and acetic acid at different temperatures on ethanol production by *Saccharomyces cerevisiae* in corn mash," *Applied Microbiology and Biotechnology*, vol. 73, pp. 1190-1196, 2007.)

Exemplary Methods

Dilution Buffer and Fluorescent Reagents

Phosphate buffered saline (PBS) at 0.1M (Sigma Aldrich) and cell culture grade $H_2O$ are also used to compare to the buffer of the invention.

The fluorescent stains, AO and PI are both nucleic stains and purchased from Biolegend (San Diego, Calif.). AO is a cationic membrane-permeable dye, when used alone, labels all cells with a green fluorescence, whereas PI is an intact membrane-impermeable dye that readily penetrates membrane-compromised nonviable cells, which produces an orange fluorescence. (Foglieni, et al., "Fluorescent dyes for cell viability: an application on prefixed conditions," *Histochemical Cell Biology*, vol. 115, pp. 223-229, 2001; Ling, et al., "Classification of larval circulating hemocytes of the silkworm *Bombyx mori*, by acridine orange and propidium iodide staining," *Histochemical Cell Biology*, vol. 120, pp. 505-511, 2003; Mascotti, et al., "HPC viability measurement: trypan blue versus acridine orange and propidium iodide," *Transfusion*, vol. 40, pp. 693-696, 2000; Solomon, et al., "Factors influencing cord blood viability assessment before cryopreservation," *Transfusion*, vol. 50, pp. 820-830, 2010; Wallen, et al., "Comparison of Two Flow Cytometric Assays for Cellular RNA-Acridine Orange and Propidium Iodide," *Cytometry*, vol. 3, pp. 155-160, 1980.) Since a significant part of AO emission spectrum overlaps the excitation of PI and both dyes are located in the nucleus in nonviable cells, fluorescence resonance energy transfer (FRET) occurs when AO and PI are utilized simultaneously. FRET is a quantum mechanical phenomenon, where radiationless energy is transferred from a donor (AO) to an acceptor (PI). In this case, when AO is excited with high quantum yield, the fluorescence energy is transferred to excite PI in nonviable cells, which quenches their AO signals. (Gordon, et al., "Quantitative Fluorescence Resonance Energy Transfer Measurments Using Fluorescence Microscopy," Biophysical Journal, vol. 74, pp. 2702-2713, 1998; Koksch, et al., "Fluorescence resonance energy transfer as a new method for the epitope-specific characterization of anti-platelet antibodies," *Journal of Immunological Methods*, vol. 187, pp. 53-67, 1995; Periasamy, "Fluorescence resonance energy transfer microscopy: a mini review," *Journal of Biomedical Optics*, vol. 6, pp. 287-291, 2201; Selvin et al., "Luminescence energy transfer using a terbium chelate: Improvements on fluorescence energy transfer," *Proceedings National Academy of Science*, vol. 91, pp. 10024-10028, 1994.) The special optical property of AOPI combination allows a clear differentiation between viable and nonviable cells.

Yeast Sample Preparation

The yeast and corn mash mixtures are provided by Lincolnway Energy (Nevada, Iowa). Seven yeast and corn mash mixtures are collected from various fermenters for concentration and viability measurement: before fermentation [2.65 h and 8 h (sample 1-2)] and during fermentation [2.5 h, 10 h, 39 h, 45 h, and 55 h (sample 3-7)] into a 500 ml polypropylene bottle [INFORMATION from biofuel contact]. The ethanol percentage and pH values are measured for each sample, which are [information needed]. Each sample is diluted 1:20 (v/v) with the dilution buffer, PBS, and cell culture grade $H_2O$ into a 50 ml centrifuge tube. Since the yeast mixture is a slushy solution, the bottle must be shaken well before dilution.

Cellometer® Vision Platform and Disposable Counting Chamber

Figure 11:
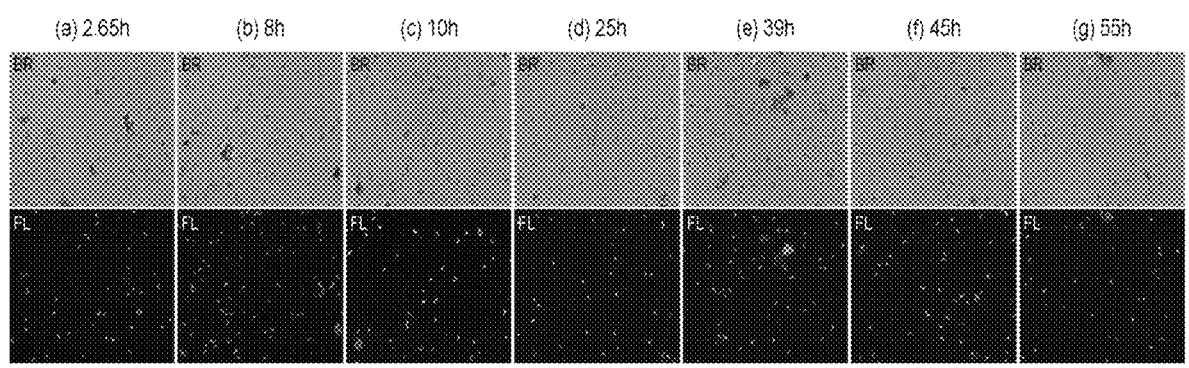
FIG. 11 depicts a series of fluorescent images of 7 fermentation samples at different stages.

The Cellometer® Vision utilizes one bright-field and two fluorescence channels to perform image cytometric analysis (FIG. 11). For the AO channel, the excitation and emission filter set is 475 nm and 535 nm, respectively. For the PI channel, the excitation and emission filter set is 540 nm and 670 nm, respectively. The Cellometer system automatically switches between the two channels to measure viable and nonviable cell concentration and generates viability for each sample.

Figure 12:
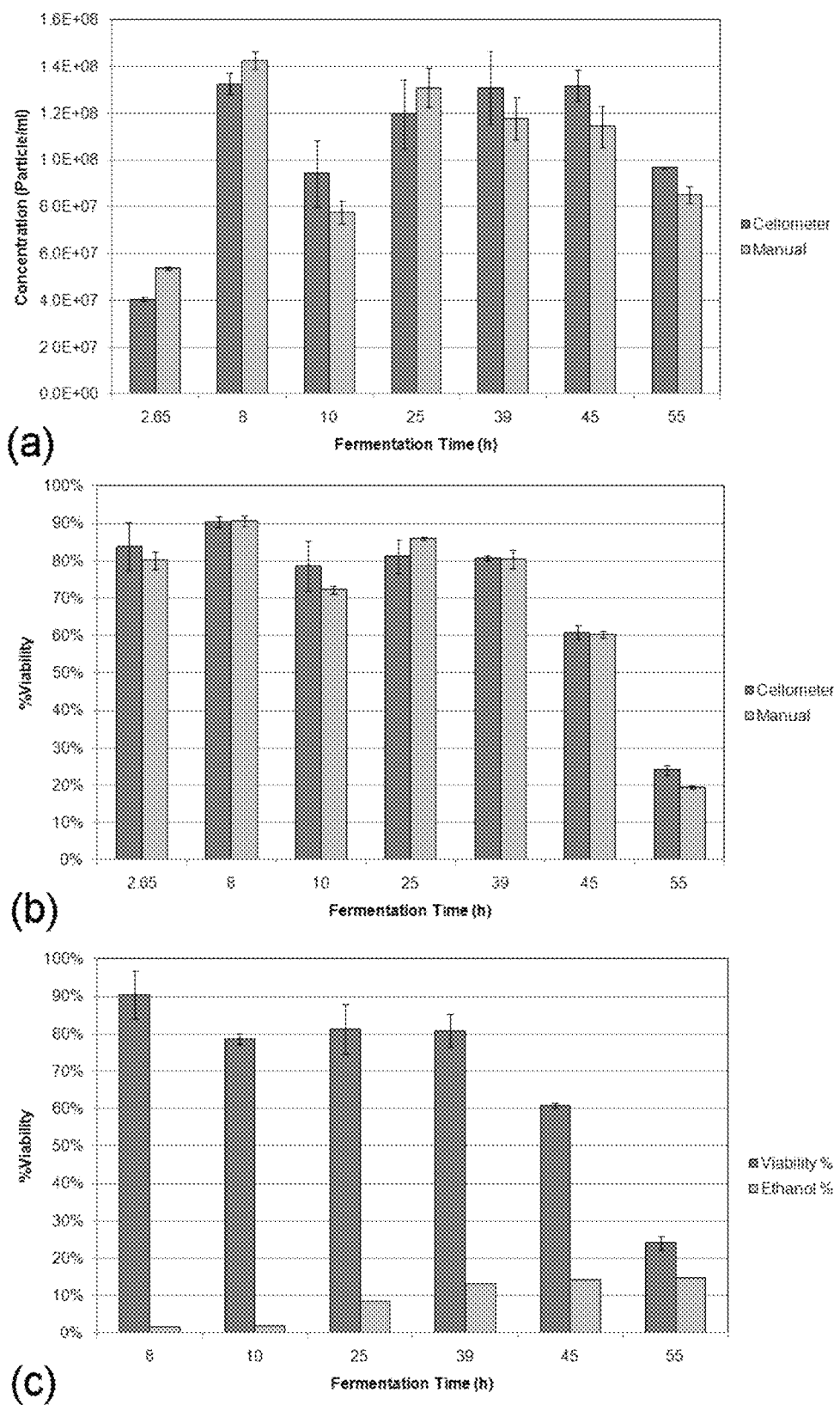
FIG. 12 depicts plots of (a) concentration and (b) viability in respect to fermentation duration for both the invention and manual counting method. (c) The plot shows the relationship between viability of yeasts versus the percentage of ethanol content in the fermented samples.

The disposable counting chamber holds precisely 20 µL of samples (FIG. 12). Four separate areas are imaged and analyzed on the counting chamber, which are performed by the counting algorithm to produce accurate and consistent concentration results.

Buffer Selection

Fluorescence signals of yeast and corn mash mixtures diluted in Nexcelom dilution buffer, PBS, and cell culture grade $H_2O$ (described above) are compared to select the optimal buffer for concentration and viability measurements. Yeast sample 2 (10 µL) is randomly selected and stained with 10 µg/mL of AOPI mixture (10 µL) to examine the signal-to-background ratio.

Fluorescent Dye Concentration Optimization

The concentration of AO and PI are optimized by performing a concentration series of both dyes in the selected optimized buffer. Both dyes are tested at 20, 10, 5, 2.5, and 1.25 µg/mL (final concentration) using the yeast sample 2 by mixing 10 µL of yeasts and 10 µL of dye, where an optimal concentration should result in bright AO fluorescence signal or high signal-to-background ratio for viable cells and dim for nonviable due to the quenching effect from PI. The nonviable cells should be bright in the PI channel, and the viable cells should be dim.

Concentration and Viability Measurement Protocol

After premixing the dilution buffer with yeast samples, the centrifuge tube is mixed by inverting back and forth 10 times. Each yeast sample (10 µL) is then mixed with 10 µL of AOPI mixture at 2.5 µg/mL, and is allowed to incubate for 2-3 min. The stained yeast sample (20 µL) is then pipetted into a cell counting chamber and is allowed to settle. Each sample is then counted and analyzed using the Cellometer® Vision in triplicates.

Manual Hemacytometer Counting Method

The images captured from the Cellometer® Vision platform are counted in two Cellometer counting chambers manually for each of the seven samples. The concentration and viability results are then compared to the automated counting from the software.

REFERENCES

[1] D. Antoni, V. V. Zverlov, and W. H. Schwarz, "Biofuel from microbes," *Applied Microbiology Biotechnology*, vol. 77, pp. 23-35, 2007.

[2] A. A. Vertés, M. Inui, and H. Yukawa, "Technological Options for Biological Fuel Ethanol," *Journal of Molecular Microbiology and Biotechnology*, vol. 15, pp. 16-30, 2008.

[3] L. C. Basso, H. V. d. Amorim, A. J. d. Oliveira, and M. L. Lopes, "Yeast selection for fuel ethanol production in Brazil," *FEMS Yeast Research*, vol. 8, pp. 1155-1163, 2008.

[4] S. Nikolić, L. Mojović, M. Rakin, D. Pejin, and V. Nedović, "Effect of different fermentation parameters on bioethanol production from corn meal hydrolyzates by free and immobilized cells of *Saccharomyces cerevisiae* var. *ellipsoideus*," *Journal of Chemical Technological Biotechnology* vol. 84, pp. 497-503, 2009.

[5] W. R. Gibbons and S. R. Hughes, "Integrated biorefineries with engineered microbes and high-value co-products for profitable biofuels production," *In Vitro Cellular & Developmental Biology-Plant*, vol. 45, pp. 218-228, 2009.

[6] X. H. Hu, M. H. Wang, T. Tan, J. R. Li, H. Yang, L. Leach, R. M. Zhang, and Z. W. Luo, "Genetic Dissection of Ethanol Tolerance in the Budding Yeast *Saccharomyces cerevisiae*," *Genetics*, vol. 175, pp. 1479-1487, 2007.

[7] J. L. Argueso, M. F. Carazzolle, P. A. Mieczkowski, F. M. Duarte, O. V. C. Netto, S. K. Missawa, F. Galzerani, G. G. L. Costa, R. O. Vidal, M. F. Noronha, M. Dominska, M. G. S. Andrietta, S. R. Andrietta, A. F. Cunha, L. H. Gomes, F. C. A. Tavares, A. R. Alcarde, F. S. Dietrich, J. H. McCusker, T. D. Petes, and G. A. G. Pereira, "Genome structure of a *Saccharomyces cerevisiae* strain widely used in bioethanol production," *Genome Research*, vol. 19, pp. 2258-2270, 2009.

[8] J. M. Eksteen, P. v. Rensburg, R. R. C. Otero, and I. S. Pretorius, "Starch Fermentation by Recombinant *Saccharomyces cerevisiae* Strains Expressing the a-Amylase and Glucoamylase Genes From *Lipomyces Kononenkoae* and *Saccharomycopsis fibuligera*," *Biotechnology and Bioengineering*, vol. 84, pp. 639-646, 2003.

[9] J. T. Trevors, R. L. Merrick, I. Russell, and G. G. Stewart, "A Comparison of Methods for Assessing Yeast Viability," *Biotechnology Letters*, vol. 5, pp. 131-134, 1983.

[10] B. Hernlem and S.-S. Hua, "Dual Fluorochrome Flow Cytometric Assessment of Yeast Viability," *Current Microbiology*, p. Published Online, 2010.

[11] W. L. Chang, H. C. v. d. Heyde, and B. S. Klein, "Flow cytometric quantitation of yeast a novel technique for use in animal model work and in vitro immunologic assays," *Journal of Immunological Methods*, vol. 211, pp. 51-63, 1998.

[12] D. Deere, J. Shen, G. Vesey, P. Bell, P. Bissinger, and D. Veal, "Flow Cytometry and Cell Sorting for Yeast Viability Assessment and Cell Selection," *Yeast*, vol. 14, pp. 147-160, 1998.

[13] J. C. Bouchez, M. Cornu, M. Danzart, J. Y. Leveau, F. Duchiron, and M. Bouix, "Physiological Significance of the Cytometric Distribution of Fluorescent Yeasts After Viability Staining," *Biotechnology and Bioengineering*, vol. 86, pp. 520-530, 2004.

[14] P. Malacrinó, G. Zapparoli, S. Torriani, and F. Dellaglio, "Rapid detection of viable yeasts and bacteria in wine by flow cytometry," *Journal of Microbiological Methods*, vol. 45, pp. 127-134, 2001.

[15] K. W. Ng, D. T. W. Leong, and D. W. Hutmacher, "The Challenge to Measure Cell Proliferation in Two and Three Dimensions," *Tissue Engineering*, vol. 11, pp. 182-191, 2005.

[16] S. E. Szabo, S. L. Monroe, S. Fiorino, J. Bitzan, and K. Loper, "Evaluation of an Automated Instrument for Viability and Concentration Measurements of Cryopreserved Hematopoietic Cells," *Laboratory Hematology*, vol. 10, pp. 109-111, 2004.

[17] H. M. Davey and D. B. Kell, "Flow Cytometry and Cell Sorting of Heterogeneous Microbial Populations: the Importance of Single-Cell Analyses," *Microbiological Reviews*, vol. 60, pp. 641-696, 1996.

[18] A. D. Michelson, "Flow Cytometry: A Clinical Test of Platelet Function," *Blood*, vol. 87, pp. 4925-4936, 1996.

[19] M. J. Henry-Stanley, R. M. Garni, and C. L. Wells, "Adaptation of FUN-1 and Calcofluor white stains to assess the ability of viable and nonviable yeast to adhere to and be internalized by cultured mammalian cells," *Journal of Microbiological Methods*, vol. 59, pp. 289-292, 2004.

[20] S. M. V. Zandycke, O. Simal, S. Gualdoni, and K. A. Smart, "Determination of Yeast Viability Using Fluorophores," *Journal of American Society of Brewing Chemists*, vol. 61, pp. 15-22, 2003.

[21] L. M. King, D. O. Schisler, and J. J. Ruocco, "Epifluorescent Method for Detection of Nonviable Yeast," *Journal of American Society of Brewing Chemists*, vol. 39, pp. 52-54, 1981.

[22] R. McCaig, "Evaluation of the Fluorescent Dye 1-Anilino-8-Naphthalene Sulfonic Acid for Yeast Viability Determination," *Journal of American Society of Brewing Chemists*, vol. 48, pp. 22-25, 1990.

[23] M. Nikolova, I. Savova, and M. Marinov, "An Optimised Method for Investigation of the Yeast Viability by Means of Fluorescent Microscopy," *Journal of Culture Collections*, vol. 3, pp. 66-71, 2002.

[24] T. Zhang and H. H. P. Fang, "Quantification of *Saccharomyces cerevisiae* viability using BacLight," *Biotechnology Letters*, vol. 26, pp. 989-992, 2004.

[25] M. L. Slater, "Rapid Nuclear Staining Method for *Saccharomyces cerevisiae*," *Journal of Bacteriology*, vol. 126, pp. 1339-1341, 1976.

[26] K.-B. Oh and H. Matsuoka, "Rapid viability assessment of yeast cells using vital staining with 2-NBDG, a fluorescent derivative of glucose," *International Journal of Food Microbiology*, vol. 76, pp. 47-53, 2002.

[27] D. Lloyd and A. J. Hayes, "Vigour, vitality and viability of microorganisms," *FEMS Microbiology Letters*, vol. 133, pp. 1-7, 1995.

[28] B. Rodriguez-Porrata, M. Novo, J. Guillamón, N. Rozès, A. Mas, and R. C. Otero, "Vitality enhancement of the rehydrated active dry wine yeast," *International Journal of Food Microbiology*, vol. 126, pp. 116-122, 2008.

[29] D. A. Abbott and W. M. Ingledew, "Buffering capacity of whole corn mash alters concentrations of organic acids required to inhibit growth of *Saccharomyces cerevisiae* and ethanol production," *Biotechnology Letters*, vol. 26, pp. 1313-1316, 2004.

[30] R. Devantier, S. Pedersen, and L. Olsson, "Characterization of very high gravity ethanol fermentation of corn mash. Effect of glucoamylase dosage, pre-saccharification and yeast strain," *Applied Microbiology and Biotechnology*, vol. 68, pp. 622-629, 2005.

[31] S. Y. Lai, P. Koppikar, S. M. Thomas, E. E. Childs, A. M. Egloff, R. R. Seethala, B. F. Branstetter, W. E. Gooding, A. Muthukrishnan, J. M. Mountz, V. W. Y. Lui, D. M. Shin, S. S. Agarwala, R. Johnson, L. A. Couture, E. N. Myers, J. T. Johnson, G. Mills, A. Argiris, and J. R. Grandis, "Intratumoral Epidermal Growth Factor Receptor Antisense DNA Therapy in Head and Neck Cancer: First Human Application and Potential Antitumor Mechanisms," *Journal of Clinical Oncology*, vol. 27, pp. 1235-1242, March 2009.

[32] S. L. Nott, Y. F. Huang, X. D. Li, B. R. Fluharty, X. Qiu, W. V. Welshons, S. Yeh, and M. Muyan, "Genomic Responses from the Estrogen-responsive Element-dependent Signaling Pathway Mediated by Estrogen Receptor alpha Are Required to Elicit Cellular Alterations," *Journal of Biological Chemistry*, vol. 284, pp. 15277-15288, May 2009.

[33] M. Qiao, Q. W. Zhao, C. F. Lee, L. R. Tannock, E. J. Smart, R. G. LeBaron, C. F. Phelix, Y. Rangel, and R. Asmis, "Thiol Oxidative Stress Induced by Metabolic Disorders Amplifies Macrophage Chemotactic Responses and Accelerates Atherogenesis and Kidney Injury in LDL Receptor-Deficient Mice," *Arteriosclerosis Thrombosis and Vascular Biology*, vol. 29, pp. 1779-U139, November 2009.

[34] R. J. Rounbehler, W. M. Li, M. A. Hall, C. Y. Yang, M. Fallahi, and J. L. Cleveland, "Targeting Ornithine Decarboxylase Impairs Development of MYCN-Amplified Neuroblastoma," *Cancer Research*, vol. 69, pp. 547-553, January 2009.

[35] 0. C. Shanks, C. A. Kelty, M. Sivaganesan, M. Varma, and R. A. Haugland, "Quantitative PCR for Genetic Markers of Human Fecal Pollution," *Applied and Environmental Microbiology*, vol. 75, pp. 5507-5513, September 2009.

[36] A. Stengel, M. Goebel, I. Yakubov, L. X. Wang, D. Witcher, T. Coskun, Y. Tache, G. Sachs, and N. W. G. Lambrecht, "Identification and Characterization of Nesfatin-1 Immunoreactivity in Endocrine Cell Types of the Rat Gastric Oxyntic Mucosa," *Endocrinology*, vol. 150, pp. 232-238, January 2009.

[37] N. Bioscience, "Simpe, Fast and Consistent Determination of Yeast Viability using Oxonol," in *Application Focus: Cellometer Vision 10×*, pp. 1-2.

[38] I. S. Pretorius, M. d. Toit, and P. v. Rensburg, "Designer Yeasts for the Fermentation Industry of the $21^{st}$ Century," *Food Technology Biotechnology*, vol. 41, pp. 3-10, 2003.

[39] T. Graves, N. V. Narendranath, K. Dawson, and R. Power, "Effect of pH and lactic or acetic acid on ethanol productivity by *Saccharomyces cerevisiae* in corn mash," *Journal of Industrial Microbiology and Biotechnology*, vol. 33, pp. 469-474, 2006.

[40] T. Graves, N. V. Narendranath, K. Dawson, and R. Power, "Interaction effects of lactic acid and acetic acid at different temperatures on ethanol production by *Saccharomyces cerevisiae* in corn mash," *Applied Microbiology and Biotechnology*, vol. 73, pp. 1190-1196, 2007.

[41] C. Foglieni, C. Meoni, and A. M. Davalli, "Fluorescent dyes for cell viability: an application on prefixed conditions," *Histochemical Cell Biology*, vol. 115, pp. 223-229, 2001.

[42] E. Ling, K. Shirai, R. Kanekatsu, and K. Kiguchi, "Classification of larval circulating hemocytes of the silkworm *Bombyx mori*, by acridine orange and propidium iodide staining," *Histochemical Cell Biology*, vol. 120, pp. 505-511, 2003.

[43] K. Mascotti, J. McCullough, and S. R. Burger, "HPC viability measurement: trypan blue versus acridine orange and propidium iodide," *Transfusion*, vol. 40, pp. 693-696, 2000.

[44] M. Solomon, J. Wofford, C. Johnson, D. Regan, and M. H. Creer, "Factors influencing cord blood viability assessment before cryopreservation," *Transfusion*, vol. 50, pp. 820-830, 2010.

[45] C. A. Wallen, R. Higashikubo, and L. A. Dethlefsen, "Comparison of Two Flow Cytometric Assays for Cellular RNA-Acridine Orange and Propidium Iodide," *Cytometry*, vol. 3, pp. 155-160, 1980.

[46] G. W. Gordon, G. Berry, X. H. Liang, B. Levine, and B. Herman, "Quantitative Fluorescence Resonance Energy Transfer Measurments Using Fluorescence Microscopy," *Biophysical Journal*, vol. 74, pp. 2702-2713, 1998.

[47] M. Koksch, G. Rothe, V. Kiefel, and G. Schmitz, "Fluorescence resonance energy transfer as a new method for the epitope-specific characterization of anti-platelet antibodies," *Journal of Immunological Methods*, vol. 187, pp. 53-67, 1995.

[48] A. Periasamy, "Fluorescence resonance energy transfer microscopy: a mini review," *Journal of Biomedical Optics*, vol. 6, pp. 287-291, 2201.

[49] P. R. Selvin and J. E. Hearst, "Luminescence energy transfer using a terbium chelate: Improvements on fluorescence energy transfer," *Proceedings National Academy of Science*, vol. 91, pp. 10024-10028, 1994.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

What is claimed is:

1. A method for measuring a concentration of yeast cells, comprising:
    staining a sample to be tested for yeast cell concentration with a dye under a buffer condition having a pH of about 10 to about 12.5;
    acquiring a fluorescent image of the dye-stained sample;
    analyzing the fluorescent image of the dye-stained sample to determine the concentration of viable yeast cells.

2. The method of claim 1, wherein the dye is selected from the group consisting of Acridine Orange, SYTO 9, DAPI, Hescht, Calcofluor White, Propidium Iodide, Ethidium Bromide, Oxonol, Mg-ANS.

3. The method of claim 1, wherein the buffer condition has a pH of about 10.5 to about 12.

4. The method of claim 1, wherein the sample to be tested for yeast viability is a sample from a biofuel fermentation process.

5. The method of claim 4, wherein the biofuel comprises ethanol or butanol.

6. The method of claim 4, wherein the sample to be tested for yeast viability comprises debris of corn mash or sugar cane.

7. The method of claim 1, wherein the yeast is the species of *Saccharomyces cerevisiae*.

8. The method of claim 1, wherein the dye is Acridine Orange having a concentration of about 1 µg/mL to about 5 µg/mL.

9. A method for determining yeast viability, comprising:
    staining a sample to be tested for yeast viability with a first dye and with a second dye under a buffer condition having a pH of about 10 to about 12.5;
    acquiring a fluorescent image of the first dye-stained sample;
    acquiring a fluorescent image of the second dye-stained sample; and
    comparing the fluorescent image of the first dye-stained sample and the fluorescent image of the second dye-stained sample to determine yeast viability.

10. The method of claim 9, wherein the first dye is selected from the group consisting of Acridine Orange, SYTO 9, DAPI, Hescht, Calcofluor White and the second dye is selected from the group consisting of Propidium Iodide, Ethidium Bromide, Oxonol, Mg-ANS.

11. The method of claim 9, wherein the first dye is Acridine Orange and the second dye is Propidium Iodide.

12. The method of claim 9, wherein the buffer condition has a pH of about 10.5 to about 12.

13. The method of claim 9, wherein the sample to be tested for yeast viability is a sample from a biofuel fermentation process.

14. The method of claim 13, wherein the biofuel comprises ethanol or butanol.

15. The method of claim 13, wherein the sample to be tested for yeast viability comprises debris of corn mash or sugar cane.

16. The method of claim 9, wherein the yeast is the species of *Saccharomyces cerevisiae*.

17. The method of claim 11, wherein Acridine Orange is at a concentration of about 1 µg/mL to about 5 µg/mL and Propidium Iodide is at a concentration of about 1 µg/mL to about 5 µg/mL.

18. A method for determining the concentration of viable yeast cells, comprising:
    staining a sample to be tested with a dye under a buffer condition having a pH of about 10 to about 12.5;
    acquiring at least one static fluorescent image of the dye-stained sample; and
    analyzing the at least one static fluorescent image of the dye-stained sample to determine the concentration of viable yeast cells in the sample.

19. The method of claim 18, wherein the dye is selected from the group consisting of Acridine Orange, SYTO 9, DAPI, Hescht, Calcofluor White, Propidium Iodide, Ethidium Bromide, Oxonol, Mg-ANS.

20. The method of claim 18, wherein the dye is Acridine Orange.

21. The method of claim 18, wherein the buffer condition has a pH of about 10.5 to about 12.

22. The method of claim 18, wherein the sample to be tested is a sample from a biofuel fermentation process.

23. The method of claim 22, wherein the sample to be tested for comprises debris of corn mash or sugar cane.

24. The method of claim 18, wherein the yeast is the species of *Saccharomyces cerevisiae*.

25. The method of claim 20, wherein Acridine Orange is at a concentration of about 1 μg/mL to about 5 μg/mL.

26. A method for determining yeast viability, comprising:
- staining a sample to be tested for yeast viability with Acridine Orange under a buffer condition of pH of about 10.5 to about 12.5;
- acquiring at least one static fluorescent image of the Acridine Orange-stained sample by directing an excitation light beam to the sample;
- staining a sample to be tested for yeast viability with Propidium Iodide under a buffer condition of pH of about 10.5 to about 12.5;
- acquiring at least one static fluorescent image of the Propidium Iodide-stained sample by directing an excitation light beam to the sample;
- comparing at least one static fluorescent image of the Acridine Orange-stained sample with at least one static fluorescent image of the Propidium Iodide-stained sample; and
- determining the yeast viability of the sample.

* * * * *